US011116884B2

(12) United States Patent
Toth

(10) Patent No.: US 11,116,884 B2
(45) Date of Patent: Sep. 14, 2021

(54) INTEGRATED SYSTEM FOR ASSESSING WOUND EXUDATES

(71) Applicant: ConvaTec Technologies Inc., Las Vegas, NV (US)

(72) Inventor: Landy Toth, Newtown, PA (US)

(73) Assignee: ConvaTec Technologies Inc., Las Vegas, NV (US)

(*) Notice: Subject to any disclaimer, the term of this patent is extended or adjusted under 35 U.S.C. 154(b) by 244 days.

(21) Appl. No.: 16/237,421

(22) Filed: Dec. 31, 2018

(65) Prior Publication Data
US 2019/0134280 A1 May 9, 2019

Related U.S. Application Data

(63) Continuation of application No. 13/992,637, filed as application No. PCT/US2011/063781 on Dec. 7, 2011, now Pat. No. 10,207,031.
(Continued)

(51) Int. Cl.
A61B 5/00 (2006.01)
A61M 1/00 (2006.01)
(Continued)

(52) U.S. Cl.
CPC .......... *A61M 1/74* (2021.05); *A61B 5/14557* (2013.01); *A61B 5/412* (2013.01); *A61B 5/445* (2013.01);
(Continued)

(58) Field of Classification Search
CPC .............. A61M 1/0031; A61M 1/0025; A61M 1/0088; A61M 2205/3331; A61B 5/14557;
(Continued)

(56) References Cited

U.S. PATENT DOCUMENTS 6,511,454 B1* 1/2003 Nakao ................. A61M 1/0062
604/131
9,194,792 B2* 11/2015 Barrett ............... A61B 5/14557
(Continued)

FOREIGN PATENT DOCUMENTS

EP 3187204 A1 7/2017
EP 3643328 A1 4/2020
(Continued)

OTHER PUBLICATIONS

Canadian Patent Application No. 2,819,475 Examination Report dated Jun. 15, 2018.
(Continued)

*Primary Examiner* — Ariana Zimbouski
(74) *Attorney, Agent, or Firm* — Taft Stettinius & Hollister LLP

(57) ABSTRACT

An integrated system for assessing wound exudates from the wound of a patient is described. The system may contain functionality to detect, process and report various wound parameters. The system also may make treatment determinations based on these findings. The system may detect one or more physiological values of the wound exudates from the wound of the patient. The system may means for comparing the one or more detected physiological values to predetermined physiological values in order to obtain a comparison result in real time. The system may include a processor 15 which provides an electronic signal based on a comparison result in which the electronic signal may correspond to guidelines for treating the wound 13. The system may be integrated with other wound treatment devices, such as negative pressure wound therapy devices (NPWT) 9.

17 Claims, 12 Drawing Sheets

Related U.S. Application Data

(60) Provisional application No. 61/421,003, filed on Dec. 8, 2010.

(51) Int. Cl.
*A61B 5/1455* (2006.01)
*A61B 5/145* (2006.01)

(52) U.S. Cl.
CPC ........... *A61M 1/73* (2021.05); *A61B 5/14539* (2013.01); *A61B 5/4836* (2013.01); *A61B 5/7235* (2013.01); *A61M 1/90* (2021.05); *A61M 2205/3331* (2013.01); *A61M 2205/3389* (2013.01)

(58) Field of Classification Search
CPC ....... A61B 5/412; A61B 5/445; A61B 5/4836; A61B 5/7235
See application file for complete search history.

(56) References Cited

U.S. PATENT DOCUMENTS

| | | |
|---|---|---|
| 9,440,963 B2 | 9/2016 | Peters et al. |
| 9,526,816 B2 | 12/2016 | Toth et al. |
| 10,016,537 B2 | 7/2018 | Menon et al. |
| 10,046,096 B2 | 8/2018 | Askem et al. |
| 10,076,447 B2 | 9/2018 | Barta et al. |
| 10,076,587 B2 | 9/2018 | Locke et al. |
| 10,143,784 B2 | 12/2018 | Walton et al. |
| 10,426,670 B2 | 10/2019 | von Blucher et al. |
| 10,426,747 B2 | 10/2019 | Johnson |
| 10,426,874 B2 | 10/2019 | Chien et al. |
| 10,426,875 B2 | 10/2019 | Blott et al. |
| 10,426,938 B2 | 10/2019 | Locke et al. |
| 10,434,015 B2 | 10/2019 | Taylor et al. |
| 10,434,142 B2 | 10/2019 | Niazi et al. |
| 10,434,210 B2 | 10/2019 | Olson et al. |
| 10,434,284 B2 | 10/2019 | Hanson et al. |
| 10,449,094 B2 | 10/2019 | Donda et al. |
| D866,756 S | 11/2019 | Allen et al. |
| 10,463,760 B2 | 11/2019 | Karthikeyan et al. |
| 10,463,773 B2 | 11/2019 | Haggstrom et al. |
| 10,470,933 B2 | 11/2019 | Riesinger |
| 10,470,936 B2 | 11/2019 | Wohlgemuth et al. |
| 10,471,122 B2 | 11/2019 | Shi et al. |
| 10,471,190 B2 | 11/2019 | Locke et al. |
| 10,478,345 B2 | 11/2019 | Barta et al. |
| 10,478,346 B2 | 11/2019 | Knutson |
| 10,478,394 B2 | 11/2019 | Yu |
| 10,485,707 B2 | 11/2019 | Sexton |
| 10,485,891 B2 | 11/2019 | Andrews et al. |
| 10,485,892 B2 | 11/2019 | Hands et al. |
| 10,485,906 B2 | 11/2019 | Freedman et al. |
| 10,486,135 B2 | 11/2019 | Yang et al. |
| 10,492,956 B2 | 12/2019 | Zamierowski |
| 10,493,178 B2 | 12/2019 | Marchant et al. |
| 10,493,184 B2 | 12/2019 | Collinson et al. |
| 10,493,185 B2 | 12/2019 | Stokes et al. |
| 10,500,099 B2 | 12/2019 | Hung et al. |
| 10,500,103 B2 | 12/2019 | Croizat et al. |
| 10,500,104 B2 | 12/2019 | Sookraj |
| 10,500,173 B2 | 12/2019 | Yang et al. |
| 10,500,235 B2 | 12/2019 | Wardell |
| 10,500,300 B2 | 12/2019 | Dybe et al. |
| 10,500,301 B2 | 12/2019 | Laurensou |
| 10,500,302 B2 | 12/2019 | Holm et al. |
| 10,501,487 B2 | 12/2019 | Andrews et al. |
| 10,506,928 B2 | 12/2019 | Locke et al. |
| 10,507,141 B2 | 12/2019 | Allen et al. |
| 10,507,259 B2 | 12/2019 | Cree et al. |
| 10,512,707 B2 | 12/2019 | Whalen, III et al. |
| 10,525,170 B2 | 1/2020 | Havenstrite et al. |
| 10,532,137 B2 | 1/2020 | Pratt et al. |
| 10,532,194 B2 | 1/2020 | Locke et al. |
| 10,537,657 B2 | 1/2020 | Phillips et al. |
| 10,542,936 B2 | 1/2020 | Goldberg et al. |
| 10,543,133 B2 | 1/2020 | Shaw et al. |
| 10,543,293 B2 | 1/2020 | Suschek |
| 10,548,777 B2 | 2/2020 | Locke et al. |
| 10,549,008 B2 | 2/2020 | Yoo |
| 10,549,016 B2 | 2/2020 | Bushko et al. |
| 10,549,017 B2 | 2/2020 | Hsiao et al. |
| 10,555,838 B2 | 2/2020 | Wu et al. |
| 10,555,839 B2 | 2/2020 | Hartwell |
| 10,556,044 B2 | 2/2020 | Robinson et al. |
| 10,561,533 B2 | 2/2020 | Hoggarth et al. |
| 10,561,536 B2 | 2/2020 | Holm et al. |
| 10,568,767 B2 | 2/2020 | Addison et al. |
| 10,568,768 B2 | 2/2020 | Long et al. |
| 10,568,770 B2 | 2/2020 | Robinson et al. |
| 10,568,771 B2 | 2/2020 | MacDonald et al. |
| 10,568,773 B2 | 2/2020 | Tuck et al. |
| 10,568,983 B2 | 2/2020 | Gerdes et al. |
| 10,575,991 B2 | 3/2020 | Dunn |
| 10,575,992 B2 | 3/2020 | Sarangapani et al. |
| 10,576,037 B2 | 3/2020 | Harrell |
| 10,576,189 B2 | 3/2020 | Locke et al. |
| 10,583,042 B2 | 3/2020 | Sarangapani et al. |
| 10,583,228 B2 | 3/2020 | Shuler et al. |
| 10,589,007 B2 | 3/2020 | Coulthard et al. |
| 10,590,184 B2 | 3/2020 | Kuo |
| 10,610,414 B2 | 4/2020 | Hartwell et al. |
| 10,610,415 B2 | 4/2020 | Griffey et al. |
| 10,610,623 B2 | 4/2020 | Robinson et al. |
| 10,617,569 B2 | 4/2020 | Bonn |
| 10,617,608 B2 | 4/2020 | Shin et al. |
| 10,617,769 B2 | 4/2020 | Huang |
| 10,617,784 B2 | 4/2020 | Yu et al. |
| 10,617,786 B2 | 4/2020 | Kluge et al. |
| 10,618,266 B2 | 4/2020 | Wright et al. |
| 10,624,984 B2 | 4/2020 | Courage et al. |
| 10,625,002 B2 | 4/2020 | Locke et al. |
| 10,632,019 B2 | 4/2020 | Vitaris |
| 10,632,224 B2 | 4/2020 | Hardy et al. |
| 10,639,206 B2 | 5/2020 | Hu et al. |
| 10,639,350 B2 | 5/2020 | Arber et al. |
| 10,639,404 B2 | 5/2020 | Lichtenstein |
| 10,646,614 B2 | 5/2020 | Grinstaff et al. |
| 10,653,562 B2 | 5/2020 | Robinson et al. |
| 10,653,782 B2 | 5/2020 | Ameer et al. |
| 10,653,810 B2 | 5/2020 | Datt et al. |
| 10,653,821 B2 | 5/2020 | Nichols |
| 10,653,823 B2 | 5/2020 | Bharti et al. |
| 10,660,799 B2 | 5/2020 | Wu et al. |
| 10,660,851 B2 | 5/2020 | Millis et al. |
| 10,660,992 B2 | 5/2020 | Canner et al. |
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 | 6/2020 | Lee et al. |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |
| 10,709,760 B2 | 7/2020 | Gronberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |
| 10,736,788 B2 | 8/2020 | Locke et al. |

(56) References Cited

U.S. PATENT DOCUMENTS

| | | |
|---|---|---|
| 10,736,985 B2 | 8/2020 | Odermatt et al. |
| 10,737,003 B2 | 8/2020 | Fujisaki |
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 2001/0029956 A1 | 10/2001 | Argenta et al. |
| 2002/0143286 A1 | 10/2002 | Tumey |
| 2002/0161317 A1 | 10/2002 | Risk et al. |
| 2004/0073151 A1 | 4/2004 | Weston |
| 2005/0192548 A1 | 9/2005 | Dolliver et al. |
| 2006/0155260 A1 | 7/2006 | Blott et al. |
| 2006/0172000 A1 | 8/2006 | Cullen et al. |
| 2006/0173253 A1* | 8/2006 | Ganapathy ............ A61B 5/1468 600/310 |
| 2006/0234319 A1 | 10/2006 | Kakui et al. |
| 2007/0118096 A1 | 5/2007 | Smith et al. |
| 2007/0185426 A1 | 8/2007 | Ambrosio et al. |
| 2007/0219512 A1 | 9/2007 | Heaton et al. |
| 2007/0239078 A1 | 10/2007 | Jaeb |
| 2008/0146906 A1 | 6/2008 | Baker et al. |
| 2008/0269582 A1 | 10/2008 | Mansour et al. |
| 2008/0269651 A1* | 10/2008 | Warlick ............... A61M 1/0031 601/11 |
| 2008/0278336 A1 | 11/2008 | Ortega et al. |
| 2009/0177051 A1 | 7/2009 | Arons et al. |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0022990 A1* | 1/2010 | Karpowicz ......... A61M 1/0025 604/543 |
| 2010/0030132 A1 | 2/2010 | Niezgoda et al. |
| 2010/0030178 A1 | 2/2010 | MacMeccan et al. |
| 2010/0125233 A1 | 5/2010 | Edward S. et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2011/0015591 A1* | 1/2011 | Hanson ............ A61B 5/150251 604/318 |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2012/0071845 A1 | 3/2012 | Hu et al. |
| 2012/0129269 A1 | 5/2012 | Choi, II et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0065751 A1 | 3/2017 | Toth |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |

(56) References Cited

U.S. PATENT DOCUMENTS

| | | |
|---|---|---|
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | MacPhee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | MacPhee et al. |
| 2019/0388589 A1 | 12/2019 | MacPhee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |

(56) References Cited

U.S. PATENT DOCUMENTS

| | | |
|---|---|---|
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizuri et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0237564 A1 | 7/2020 | Hammond et al. |
| 2020/0237816 A1 | 7/2020 | Lait |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289328 A1 | 9/2020 | Luckemeyer et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306094 A1 | 10/2020 | Kushnir et al. |
| 2020/0315853 A1 | 10/2020 | Waite |
| 2020/0315854 A1 | 10/2020 | Simmons et al. |
| 2020/0316271 A1 | 10/2020 | Lin |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |

(56) References Cited

U.S. PATENT DOCUMENTS

| | | |
|---|---|---|
| 2020/0338228 A1 | 10/2020 | Kharkar et al. |
| 2020/0338243 A1 | 10/2020 | Harrison et al. |

FOREIGN PATENT DOCUMENTS

| | | |
|---|---|---|
| EP | 3643330 A1 | 4/2020 |
| EP | 3643331 A1 | 4/2020 |
| EP | 3669838 A1 | 6/2020 |
| EP | 3669843 A1 | 6/2020 |
| EP | 3669844 A1 | 6/2020 |
| GB | 2579211 A | 6/2020 |
| GB | 2579368 A | 6/2020 |
| JP | 2004265269 A | 9/2004 |
| JP | 2005293241 A | 10/2005 |
| JP | 2009525776 A | 7/2009 |
| JP | 2010510837 A | 4/2010 |
| JP | 2010531700 A | 9/2010 |
| WO | WO-2004040273 A1 | 5/2004 |
| WO | 2005018543 A2 | 3/2005 |
| WO | WO-2007062024 A1 | 5/2007 |
| WO | WO-2007092397 A2 | 8/2007 |
| WO | WO-2008048481 A2 | 4/2008 |
| WO | WO-2008064502 A1 | 6/2008 |
| WO | WO-2008100671 A1 | 8/2008 |
| WO | WO-2009039203 A2 | 3/2009 |
| WO | WO-2009141820 A1 | 11/2009 |
| WO | WO-2010011920 A2 | 1/2010 |
| WO | 2011121394 A1 | 10/2011 |
| WO | 2011135284 A1 | 11/2011 |
| WO | 2011144888 A1 | 11/2011 |
| WO | WO-2012078781 A1 | 6/2012 |
| WO | WO-2012078784 A1 | 6/2012 |
| WO | 2013015827 A2 | 1/2013 |
| WO | 2013126049 A1 | 8/2013 |
| WO | 2014014842 A1 | 1/2014 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |
| WO | 2020070231 A1 | 4/2020 |
| WO | 2020074512 A1 | 4/2020 |
| WO | 2020078993 A1 | 4/2020 |
| WO | 2020079009 A1 | 4/2020 |
| WO | 2020079330 A1 | 4/2020 |
| WO | 2020081259 A1 | 4/2020 |
| WO | 2020081391 A1 | 4/2020 |
| WO | 2020092598 A1 | 5/2020 |
| WO | 2020136555 A1 | 7/2020 |

OTHER PUBLICATIONS

Canadian Patent Application No. 2,819,475 Examination Report dated Oct. 4, 2017.
Canadian Patent Application No. 2,819,549 Office Action dated Oct. 4, 2017.
Chinese Patent Application No. 201180067100.0 First Office Action dated Jan. 28, 2015.
Chinese Patent Application No. 201180067100.0 Search Report dated Jan. 20, 2015.
Chinese Patent Application No. 201180067112.3 First Office Action dated Jun. 11, 2015.
Chinese Patent Application No. 201180067112.3 Search Report dated Jan. 20, 2014.
European Patent Application No. 11847022.8 Communication dated Feb. 10, 2017.
European Patent Application No. 11847022.8 Communication dated Sep. 2, 2016.
European Patent Application No. 11847037.6 Communication dated Jul. 21, 2016.
European Patent Application No. 11847037.6 Communication dated Jul. 23, 2015.
European Patent Application No. 11847037.6 Communication dated Mar. 22, 2017.
European Patent Application No. 11847037.6 extended European Search Report dated Aug. 21, 2014.
Japanese Patent Application No. 2013-543318 Decision of Rejection dated Dec. 10, 2015.
Japanese Patent Application No. 2013-543318 Office Action dated Nov. 4, 2014 (English language translation provided on Jul. 5, 2015 and attached herewith).
Japanese Patent Application No. 2013-543319 Office Action dated Sep. 27, 2016.
Japanese Patent Application No. 2013-543319 Office Action dated Jun. 29, 2015.
Japanese Patent Application No. 2013-543319 Office Action dated Nov. 4, 2014.

(56) References Cited

OTHER PUBLICATIONS

Japanese Patent Application No. 2016-086432 Office Action dated Mar. 14, 2017.
Japanese Patent Application No. 2017-013321 Office Action dated Jan. 9, 2018.
PCT Patent Application No. PCT/US2011/063781 International Preliminary Report on Patentability dated Jun. 12, 2013.
PCT Patent Application No. PCT/US2011/063781 International Search Report dated Mar. 21, 2012.
PCT Patent Application No. PCT/US2011/063781 Written Opinion dated Mar. 21, 2012.
PCT /US2011/063784 International Preliminary Report on Patentability dated Jun. 12, 2013.
PCT/US2011/063784 International Search Report completed Mar. 9, 2012.
PCT/US2011/063784 Written Opinion completed Mar. 9, 2012.
U.S. Appl. No. 13/992,637 Office Action dated Jan. 15, 2016.
U.S. Appl. No. 13/992,637 Office Action dated Jun. 14, 2017.
U.S. Appl. No. 13/992,637 Office Action dated May 23, 2018.
U.S. Appl. No. 13/992,637 Office Action dated May 6, 2015.
U.S. Appl. No. 13/992,637 Office Action dated Oct. 7, 2016.
U.S. Appl. No. 13/992,637 Office Action dated Sep. 25, 2017.
U.S. Appl. No. 13/992,642 Office Action dated Dec. 18, 2015.
U.S. Appl. No. 13/992,642 Office Action dated Jul. 15, 2015.
U.S. Appl. No. 13/992,642 Office Action dated Mar. 25, 2015.
U.S. Appl. No. 15/353,608 Office Action dated Dec. 13, 2017.
U.S. Appl. No. 15/353,608 Office Action dated Jun. 20, 2018.

\* cited by examiner

INTEGRATED SYSTEM FOR ASSESSING WOUND EXUDATES

CROSS-REFERENCE TO RELATED APPLICATIONS

This application is a continuation application of U.S. application Ser. No. 13/992,637, filed on Jul. 26, 2013, now issued as U.S. Pat. No. 10,207,031 on Feb. 19, 2019, which is a U.S. National Phase entry of International Application No. PCT/US2011/063781, filed on Dec. 7, 2011, which claims the benefit of the filing date of U.S. Provisional Patent Application No. 61/421,003 filed Dec. 8, 2010, the disclosure of which are hereby incorporated herein by reference.

BACKGROUND OF THE INVENTION

There is a need to autonomously monitor and assess the negative pressure wound therapy ("NPWT") process and to provide a mechanism to interrupt the NPWT therapy in cases where a contraindication develops in the patient during use. There is also a further need to improve upon certain features of NPWT devices, such as safety, functionality and intelligent, real time feedback.

Current treatment protocols for assessing wound state involve the qualitative analysis by caregivers. Often, a caregiver may assess the condition of a wound by the way it looks or smells or the overall appearance of the exudates. Many times, however, the caregiver may not be assessing the wound regularly or quantitatively. Such assessment may only occur at daily or weekly intervals, for example. A disadvantage to this treatment protocol is that the assessment is of old exudates. The physiological parameters of these exudates may change over time, when compared to their original state in the wound. Color, microbes, oxygen, and temperature all change over time, so the assessment of the exudates at a time after they have been collected is not an accurate or reliable prediction of wound condition. Additionally, the flow of exudates may be a useful tool in wound assessment. Prior assessment techniques may not offer a viable solution for monitoring wound exudates flow.

SUMMARY OF THE INVENTION

In accordance with an aspect of the invention, a system for assessing wound exudate from the wound of a patient may include a system comprising a wound treatment device, detecting means for detecting one or more values of one or more physiological parameters of the wound exudate, analyzing means for analyzing the values of the one or more physiological parameters so as to obtain an assessment of the wound exudate, and providing means for providing treatment guidelines based on the assessment, in which the wound treatment device, the detecting means, the analyzing means, and the providing means are integrated.

DETAILED DESCRIPTION

A system, apparatus and method for monitoring and assessing wound exudates are disclosed herein. The system and apparatus ("wound exudate system" or "system") allow for convenient assessment of wound exudates from a wound site and may provide real time quantitative and predictive functionality, as well as an integrated inline diagnostic solution. Also, the system may be integrated into a wound treatment device.

In addition, a system and method for collecting physiological data, and predicting wound healing outcomes based on trends of values of exudate flow rate and other characteristics are also disclosed.

Figure 1:
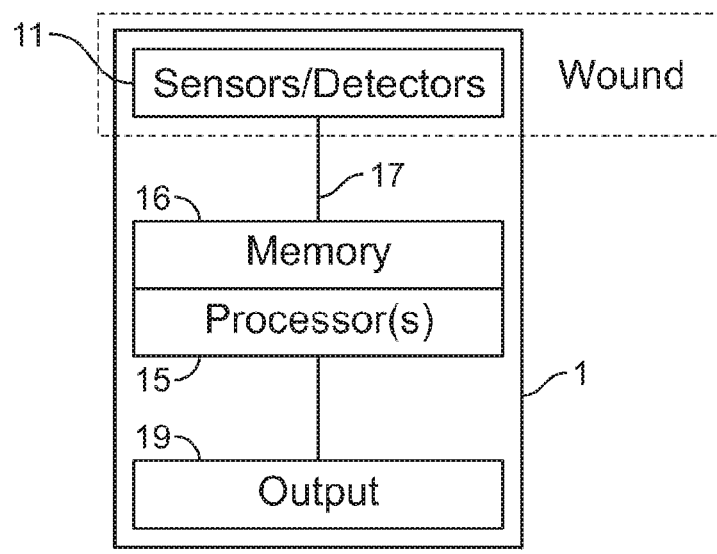
FIG. 1 is a functional block diagram representing components of a wound exudate system, in accordance with an embodiment of the present invention.

FIG. 1 is a block diagram of an embodiment of a wound exudate system 1, in accordance with the present invention. In this embodiment, sensors or detectors 11 may detect and retrieve data representing the condition of a wound. This wound data may be transferred electronically via wired or wireless means 17 to one or more processors 15. The processors may, among other things, predict wound state and other treatment solutions, based on the wound data.

Optionally, data may be stored in a memory 16. Information from the processor(s) 15 may be transmitted to an output device 19 by any means known in the art, in order to inform or alert a user about the health or state of a wound.

Figure 2:
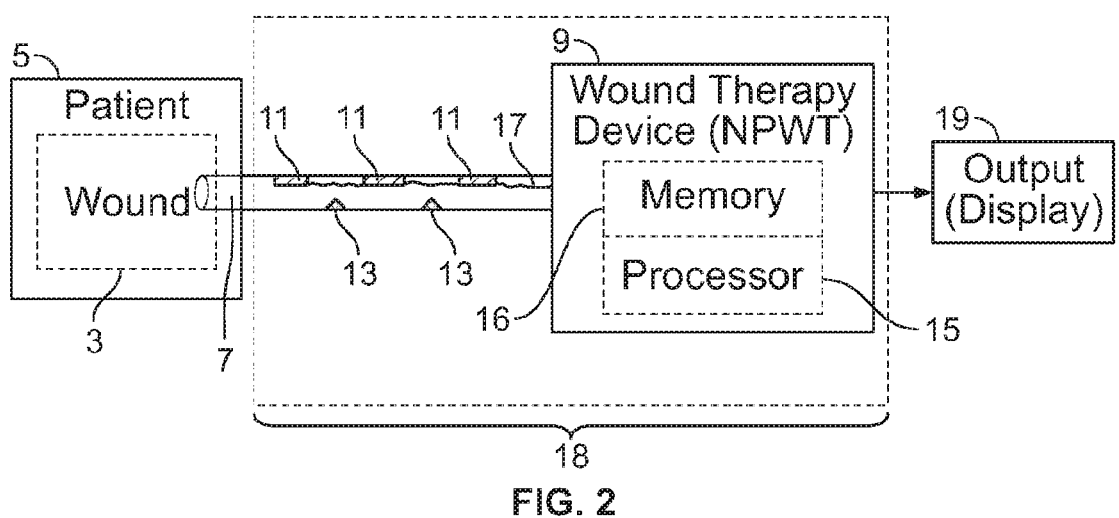
FIG. 2 shows an embodiment of a wound exudate system integrated within an NPWT device, in accordance with an embodiment of the present invention.

FIG. 2 depicts one embodiment of a wound exudate system 18. In accordance with an aspect of the present invention, the system 18 is generally in fluid communication with a wound 3 (and wound exudate) of a patient 5. Fluid communication between the system 18, and the wound 3, may be by any means known in the art, e.g., a wound drain 7 that is part of a wound therapy device 9.

The wound exudate system 18 may include one or more sensors or detectors 11, which may be used to detect various parameters, including but not limited to temperature, pH, color, viscosity and tone. These parameters are useful indicators of present wound state, and may be used in accordance with aspects of the present invention to render viable treatment options.

The wound exudate system may optionally employ one or more types of light sources 13. The light sources 13 may emit varying wavelengths of light, depending on their programmed functionality. The wavelengths of light may be emitted through the wound exudate and may be altered depending on the characteristics of the exudate itself.

The wavelengths may then be detected by the sensors or detectors 11. The wavelengths detected by the sensors or detectors 11 may represent various conditions of the wound exudate being analyzed. The sensors or detectors 11 may transmit information representative of the detected wavelengths via electronic circuitry 17, to one or more processors 15 integral within the wound exudate system 18.

The one or more processors 15 may be adapted to receive the detected wavelength data, and conduct various analyses by way of programmed processes. The processor(s) 15 may receive the wavelength data from the sensor(s) 11, and use such data in appropriate process. A determination of the process can be any type of diagnosis or categorization of wound health or healing, as well as a prescribed treatment regimen. Various information including but not limited to historical data, processes, and vector maps may be stored in a memory 16.

The determination of the process may be communicated, wirelessly or via wired means, to be displayed on an onboard or external display 19. As shown in FIG. 2, the exudate system 18 may be integrated directly into the wound therapy device 9. In this configuration, the processor 15 may be integrated into the wound therapy device, and the sensors, detectors and circuitry may be integral with a wound drain that is part of an active treatment device, or a bandage or dressing.

The system 18 may detect the presence of blood in the exudates, as well as monitor and assess other physiological values relevant to wound exudates, such as flow rate/quantity, color, bacterial traces, temperature, pH and the like.

Figure 3:
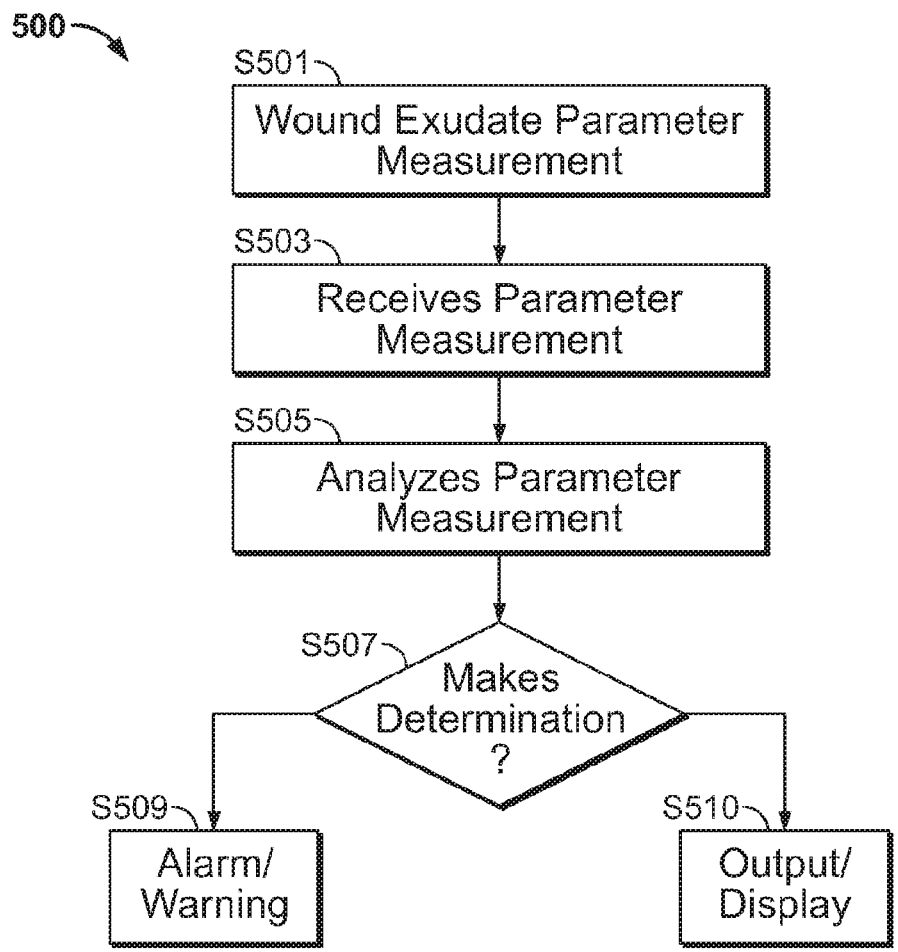
FIG. 3 is flow diagram of a wound assessment process, in accordance with an embodiment of the present invention.

FIG. 3 is a flow diagram illustrating an exemplary wound exudate system process 500. The blocks in FIG. 3 are representative of various functions of a wound exudate system, which may be combined, omitted, added, or reordered as suitable.

In block S501, sensors detect and/or measure one or more parameters of the wound exudate. Measurement Data obtained in block S501 is transmitted to and received by one or more processors in block S503. The processors then analyze the received data in block S505. Based on results of analyzing, determination (s) may be made in block S507 regarding the measurements by the sensors. Those determinations, which may include a diagnosis or treatment guideline may then be outputted via an alarm or warning in block S509, or an output display in block S510.

Integrated Structure

The wound exudates systems disclosed herein and illustrated in the attached drawings may contain various structural features. The system may be configured differently to attach to an existing wound therapy device, or be integrated directly into one of these devices. The structure of the system may also include sources of light for spectral analysis, as well as sensors or detectors for detecting the light emitted by these light sources. Detection of light at a particular wavelength after it has been emitted through wound exudate may indicate the value of a certain parameter of the exudate. The system may also include sensors for measuring non-spectral parameters such as temperature and pressure.

Figure 4:
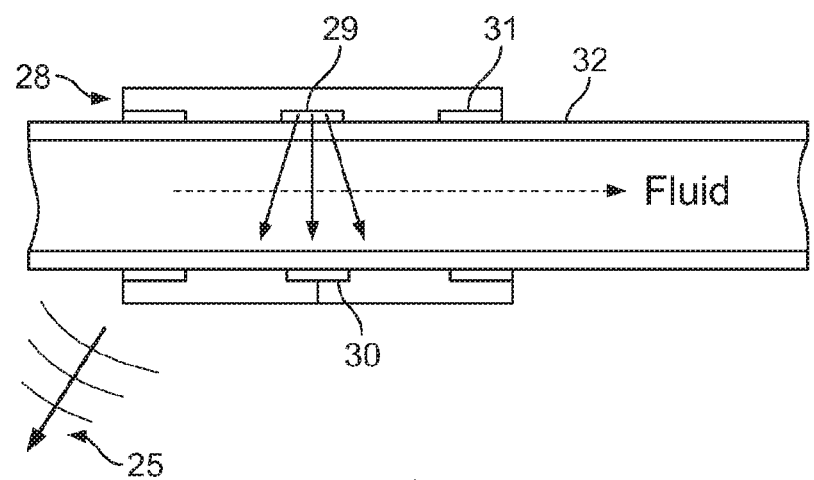
FIG. 4 depicts a cross-sectional view of a wound exudate system, in accordance with an embodiment of the present invention

FIG. 4 depicts an embodiment of a wound exudate system 28 integrated into an existing wound drain line. The system contains a light source 29 for emitting light of a certain wavelength(s) into the exudate. The system also contains a detector 30 for detecting and/or sensing the emitted wavelengths of light after it has passed through wound exudate. Amplitude of the detected wavelengths represent the spectral attributes of the exudates and may be indicative of wound state.

Additionally, the embodiment depicted by FIG. 4 depicts an optical barrier 31 disposed on the exterior of a wound drainage line 32. The optical barrier 31 is useful for avoiding ambient light from reaching the wound exudate. This increases the accuracy of the detection, as it avoids any artifacts that may be caused by light other than that emitted by the source 29.

Figure 5:
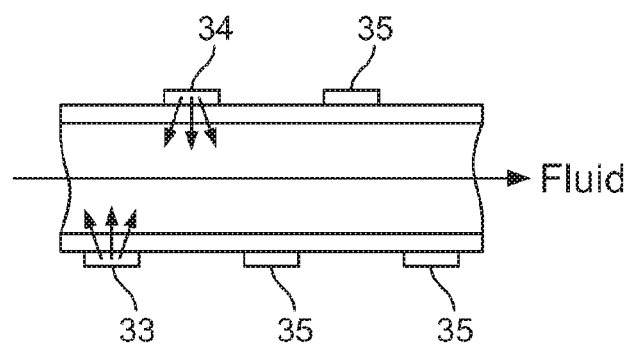
FIG. 5 depicts an embodiment of a wound exudate system containing multiple light sources and multiple detectors, in accordance with an embodiment of the present invention.

FIG. 5 depicts another alternative embodiment of the present invention, in which the system may contain multiband sources of light, including a narrowband source 33 and a broadband source 34. Multiple multiband detectors 35 may also be disposed within the system. Multiband sources and detectors may be useful for detecting various wavelengths of light and therefore different attributes of the exudates. The detectors 35 may be configured to remove unwanted ambient light and obtain more complete spectral information.

In another embodiment, which may be suitable for use in hospital setting, an exudates system may be integrated within a central suction system. In this case, the exudates system may be associated and operated in tandem with an existing central suction system, so as to warn and shutdown flow from the wound site in the case of an adverse event. In this case, the exudates system may clamp the wound drainage line in the case of an adverse event. Such an embodiment may provide a safe and low cost alternative to existing NPWT devices in a hospital setting. This mechanism may be useful in preventing inadvertent hemorrhagic crises created by undetected bleeding. In this case, the central suction unit may be pre-configured with an integrated wound monitoring system as described herein.

Figure 6:
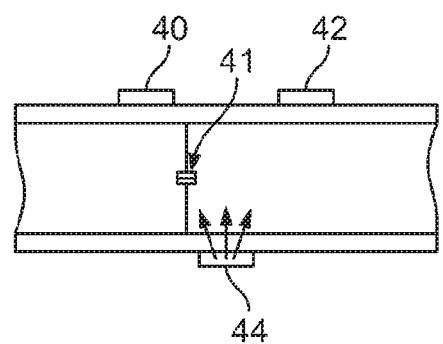
FIG. 6 depicts a wound exudate system that contains a flow disruption element, in accordance with an embodiment of the present invention.

FIG. 6 depicts an alternative embodiment of a wound exudate system that contains a flow disruption element 41 in combination with one or more detectors 40 and 42 and a source 44. The arrangement of the present embodiment may provide more accurate sensing, based on the deflection of the flow disruption element.

In one embodiment, an exudates system may comprise a fluid channel through which exudates may pass. In this case, the fluid channel may further comprise an obstruction located in the path of the exudates, as seen in FIG. 6. As exudates pass the obstruction, a disturbance in the flow is created. The behavior of the flow in and around the disturbance may be useful for measuring parameters of the flow, such as viscosity, concentration and/or composition of solid matter, etc. The disturbance in the flow can also be used to better mix the exudate, which may be useful for improving measurement accuracy. Any signal variation between detectors 40 and 42 may be related to the flow disruption element. Viscosity may also be used to determine general water content of the exudates, as well as the presence of large molecules.

Figure 8:
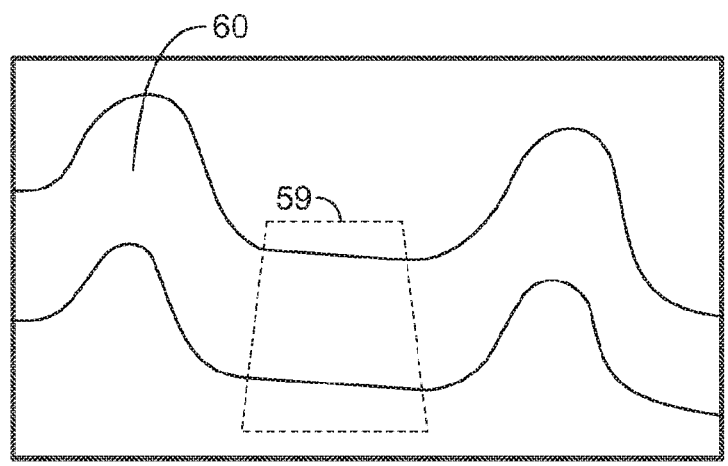
FIG. 8 depicts a wound drain tube configured with a tortuous path, in accordance with an embodiment of the present invention.
Figure 9:
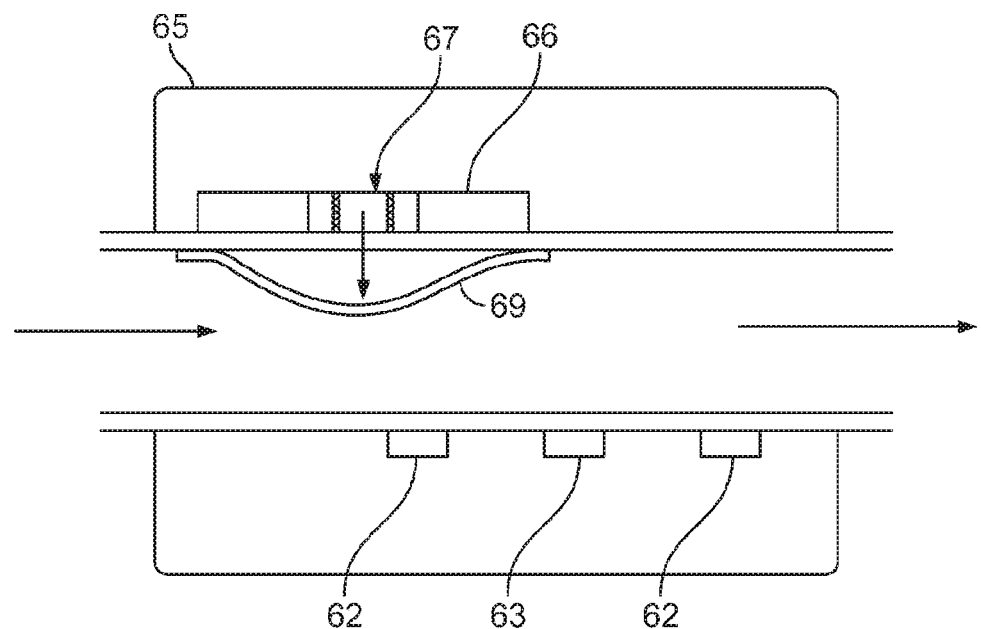
FIGS. 9 and 10 depict embodiments of a wound exudate system for pinching a wound drainage line, in accordance with an embodiment of the present invention.

A wound exudate system may also be configured with a flow drain arranged in a tortuous path 60, as seen in FIG. 8. This configuration may function to eliminate ambient light from the sensory region 59.

Figure 19:
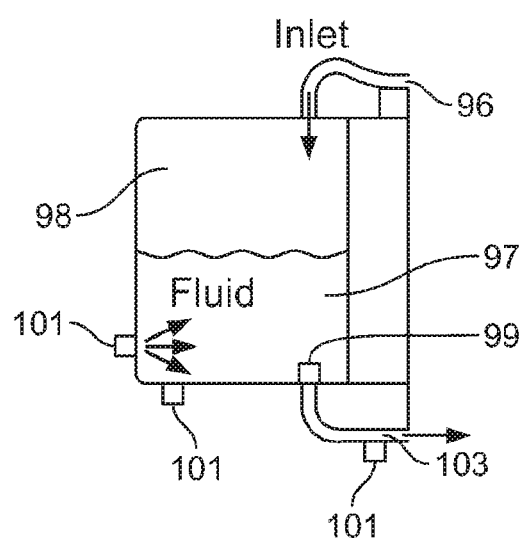
FIG. 19 depicts a wound exudate system configured within a collection chamber, in accordance with an embodiment of the present invention.
Figure 25:
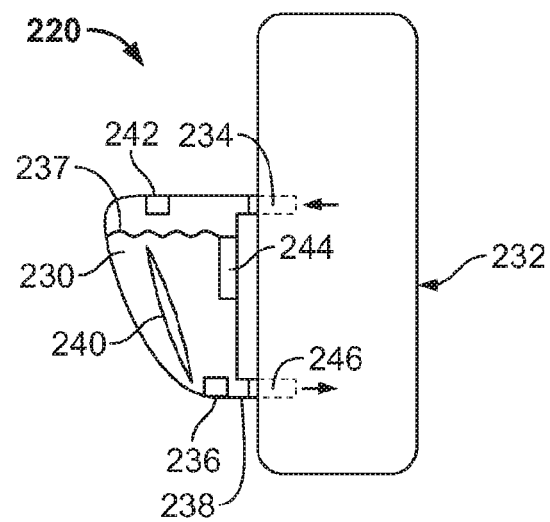
FIG. 25 illustrates an alternative embodiment of a wound exudate system disposed within an ancillary collection chamber, in accordance with an embodiment of the present invention.

In another embodiment of the present invention, an exudate assessment system may also have structures and shaped tubes in the flow path to ensure that the fluid under analysis does not mix with previously collected exudates prior to being assessed, as seen in FIGS. 8, 19 and 25.

In yet another embodiment, the exudates system may have a chamber or trap 98, as seen in FIG. 19, into which fluids can pool, or low so as to assist with obtaining more precise measurements regarding the physical state of the exudates. Measurements, such as flow rate may be taken of the pooled fluid, the flowing fluid, or both. This embodiment may be particularly useful for measuring the thermal mass of the exudate.

The exudates system may also comprise a compartment to be filled by exudates leaving the wound site as seen in FIG. 19. In this embodiment, the compartment may be suitable for isolating exudates for analysis or to periodically weigh exudates removed from the wound site so as to assess the rate of fluid removed from the wound site over time. The compartment may include an automatic means for emptying when the fluid volume reaches a set level. Alternatively, the Compartment may have an active system such as valves, to empty the compartment when the fluid reaches a set level.

In this embodiment, the exudates system may comprise one or more valves to direct and/or interrupt flow through the wound drain. In yet another embodiment, the exudates system may draw off fluid for a sample without fully interrupting flow through the fluid line. The separated fluid as indicated in FIG. 19, is analyzed within the line and allowed to remix further downstream. An alternative design may include a sampling port for caking a sample for analysis.

In an alternative embodiment, the exudates system may be integrated along an inner or outer surface of a canister or arranged, so as to mate with a canister. In this embodiment, the system may be arranged to detect the values of various physiological parameters of the exudates accumulated during use. In this case, the system may monitor and detect the weight, height, impedance, etc. of the exudates as it accumulates in the canister. Such information may be valuable for determining if an adverse event has occurred, such as the onset of bleeding. It may also be valuable for determining the overall rate of exudates removal from the wound site, thus providing predictive planning for canister changes, or even to assess wound progression from a highly exudating state to a superficially exudating state.

Changes in the rate of exudates flowing from the wound site may be indicative of a change in the wound state. In another instance, changes in the composition of the wound exudates may indicate a clinically relevant change in the wound state. Such changes in exudates removal rates may also be useful in determining how to most optimally change from one therapy to another. In one instance, a relative change from a highly exudating wound to one of a superficially exudating wound may be useful to monitor. A transition from a highly exudating wound to a superficially exudating wound may provide useful information as to when a patient may be transferred from a more expensive to a less expensive therapy. An example of an expensive therapy is NPWT, while examples of lower cost therapies are moist wound dressings or bandages.

The exudates system may comprise a sensor or series of sensors suitable for determining the values of the above properties of wound exudates.

The exudates system may also comprise one or more disposable sensors for enabling contact based measurements of the exudates. Such sensor elements may comprise acoustic, photoacoustic, electrochemical, optical, and/or impedance spectroscopic elements arranged so as to monitor values of one or more parameters of the exudates.

The sensor or sensors may be arranged so as to collect information through the outer film of a dressing or through the wall of a wound drainage line. The sensors may be temperature sensors, optical sensors, impedance sensor, electrochemical sensors (e.g.: amperometric sensors), capacitive sensors, or the like.

The exudates system may comprise any type of flow sensor known in the art for determining the quantity or rate of fluid removed from a wound site. The flow sensor may be of a contact or non-contact type. In the case of a non-contact type flow sensor, the sensor may be a level sensor, a load cell, a flow event timer, a droplet counter, a velocimeter or the like. In the case of a contact type flow sensor, the sensor may be a load cell, pressure head monitor (such as a manometer), a strain gauge, a turbine, a thermal mass sensor, pressure loss monitors, a tow line, or similar.

Any physiological parameter of wound exudates can be assessed using embodiments of the present invention. Particular parameters of interest may include, flow of wound exudates, volume rate, pH, temperature, hemoglobin concentration, color and tone.

In one embodiment, the exudates system may evaluate exudates flow rates by measuring the rate at which a collection chamber fills, as seen for example in FIGS. 19 and 25. In one embodiment the exudates system may comprise a combination of a load cell with a measurement chamber to measure flow rate and an accelerometer to monitor orientation of the measurement chamber with respect to the vertical axis, as seen in FIG. 19. Combined signals from the sensors may be used to determine the correct flow rate of exudates from the wound site independent of the orientation of the exudates system.

In yet another embodiment, the exudates system may have a chamber or trap 98, as seen in FIG. 19, into which fluids 97 may pool, or flow so as to assist with obtaining more precise measurements regarding the physical state of the exudates. Measurements, such as flow rate may be taken of the pooled fluid, the flowing fluid, or both by sensors 101. This embodiment may be particularly useful for measuring the thermal mass of the exudate.

The exudates system may also comprise a compartment 98 to be filled by exudates leaving the wound site as seen in FIG. 19. In this embodiment, the compartment 98 may be suitable for isolating exudates for analysis or to periodically weigh exudates removed from the wound site so as to assess the rate of fluid removed from the wound site over time. The compartment may include an automatic means for emptying when the fluid volume reaches a set level. Alternatively, the compartment may have an active system such as valves 99, to empty the compartment 98 when the fluid 97 reaches a set level. Fluid may enter the compartment 98 through an inflow tube 96, and exit the compartment 98, via an exit tube 103.

In this embodiment, the exudates system may comprise one or more valves 99 to direct and/or interrupt flow through the wound drain. In yet another embodiment, the exudates system may draw off fluid for a sample without fully interrupting flow through the fluid line. The separated fluid as indicated in FIG. 19, is analyzed within the line and allowed to remix further downstream. An alternative design may include a sampling port for taking a sample for analysis.

Table 1 depicts various flow rates and their potential clinical indications. By quantifying these flow rates, and assessing them together with the other physiological parameters discussed herein, an accurate prediction of wound health may be obtained.

TABLE 1

| Exudate Volume | Wound State | Clinical Relevance |
| --- | --- | --- |
| Nothing | dry wound | desiccation |
| Scant | moist wound tissue (good) | Normal |
| Somewhat | wet wound tissue | Potential maceration |
| Moderate | saturated wound tissues | Likely maceration |
| Copious | wound tissues are bathed in fluid | maceration |

Flow Rate Example

In one example of the present technology, a collection canister was built to demonstrate flow measurement using the concept illustrated by the embodiment in FIG. 25. FIG. 25 is an alternative embodiment of the present invention depicting a wound exudate system and strain gauges disposed within an ancillary collection chamber. Such measurements may be taken by one or more sensors, including but not limited to strain gauges 236, a capacitive level gauge 244, optical gauge elements 242, and electrical gauge elements 240. Standard types of gauges for measuring weight or level are well known in the art. For example a strain gauge is based on a simple electrical circuit, wherein mechanical stress caused by change in weight causes the electrical resistance of the elements to change in proportion to the weight applied. A capacitance gauge reads a different level of capacitance between two points. In the present technology, the level of fluid 237 in the chamber (e.g., the wound fluid) may have a different value of capacitance to that of air so the level of the fluid in the container may be determined. Alternatively, an optical gauge may use light to determine the distance between two points (e.g., the top of the canister and the fluid may indicate changes in the level of the fluid 237.

The system in this particular example may include a small reservoir 230 in fluid communication with a larger reservoir 232, an inlet port 234 feeding into the small reservoir 230. The small reservoir 230 was attached to the larger reservoir 232 with a flexible support 238. A strain gauge based load cell 236 was applied to the flexible support in order to measure flexure of the support during use 238. Saline was used to approximate the fluid under measurement during the study. The system was also equipped with electrical gauge elements 240, optical gauge elements 242, a capacitive level gauge 244. Therefore, the example demonstrates that individually, or if necessary in combination, different sensor types may be used to determine flow rate.

In this example, small amounts of fluid were fed through the inlet and the sensor response was recorded on a computer (PC). During injection of fluid, the reservoir was subjected to chaotic disturbances in an attempt to disrupt the sensor readings. Such inputs would be typical of movements experienced by the device during a mobile use scenario. The response data was filtered using finite impulse response and infinite impulse response filters. The filters were used to remove movement artifacts and recover a usable signal from the input.

In general, the signal detected the system was related to the weight of the small reservoir. This is in turn related to the time integral of the flow rate of fluid into the container. Thus the flow rate was able to be extracted from the reservoir weight signal.

A valve 246 was used between the small reservoir and the large reservoir in order to drain and reset the reservoir when it became too full. The flow dynamics of this emptying process can be used to determine viscosity related information about the fluid under study.

Figure 26:
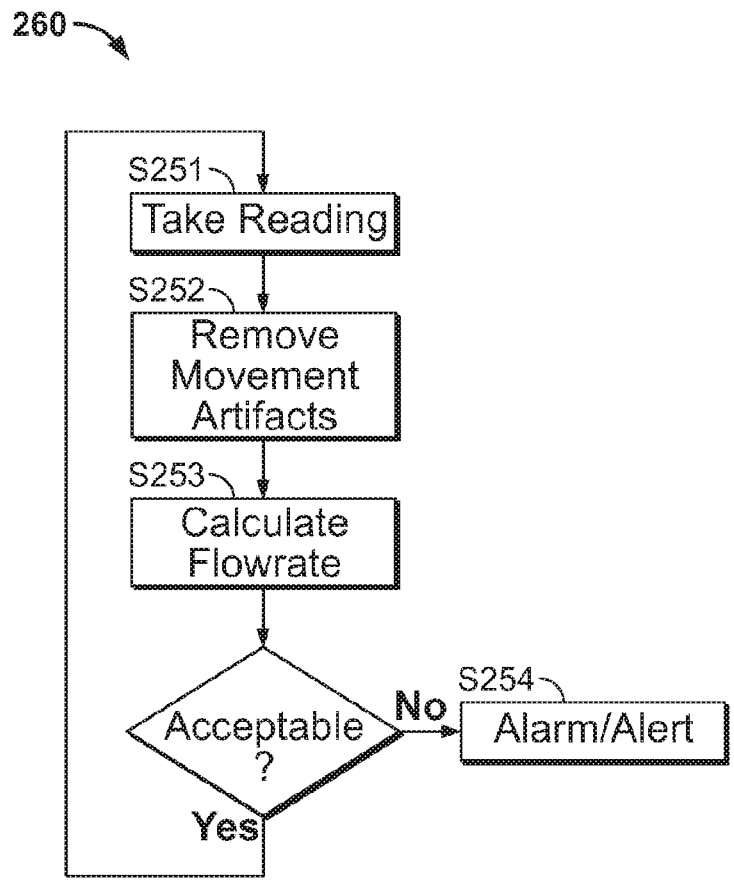
FIG. 26 is a flow diagram illustrating an exemplary process for obtaining flow measurements of wound exudate measurements, in accordance with an embodiment of the present invention.
Figure 27:
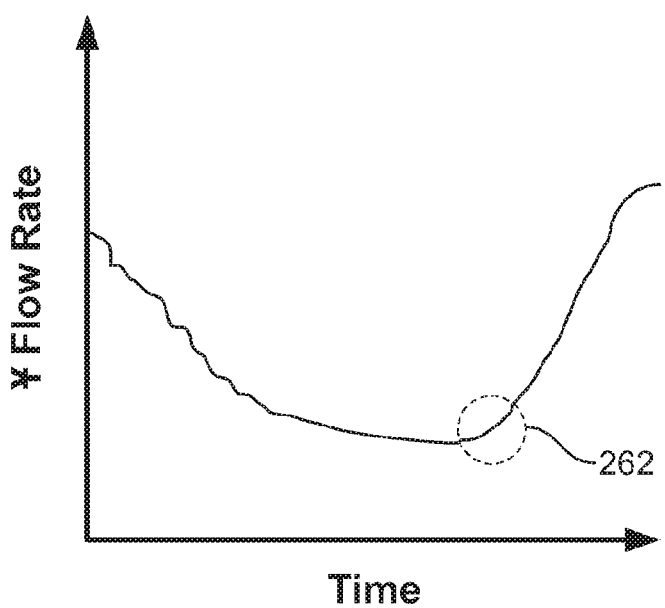
FIG. 27 is a two-dimensional graph depicting flow rate measurements, in accordance with an embodiment of the present invention.

FIG. 26 depicts a process 260 that is further related to flow measurement of FIG. 19 and FIG. 25. The process 260 includes (1) taking a flow reading in block S251; (2) removing any movement artifacts in block S252 (1); and (3) calculating a flow rate in block S253 based on methods known in the art and, in particular, those disclosed herein. If the calculated flow rate is acceptable, measurements will continue to be taken. If the flow rate is not acceptable an alarm or alert is triggered in block S254. The flow rates calculated in process 260 can also be mapped in a graph as seen FIG. 27. As with process 260, the spectral maps described here in various values along the flow rate map may indicate an onset of infection and/or bleeding, i.e., 262.

Exudate flow rate, which may be measured by the methods described herein, or any of the methods known to those of ordinary skill in the art is a reliable predictor of wound health. In certain embodiments of the present invention, flow rate values, and changes in flow rate values may be detected through various means and may also be useful in determining how to most optimally change from one therapy to another. In one instance, a relative change from a highly exudating wound to one of a superficially exudating wound may be useful to monitor. A transition from a highly exudating wound to a superficially exudating wound may provide useful information as to when a patient can be transferred from a more expensive to a less expensive therapy. An example of an expensive therapy is NPWT, while an example of a lower cost therapy is moist wound dressings or bandages. In one instance, changes in the rate of exudates flowing from the wound site may be indicative of a change in the wound state. In another instance, changes in the composition of the wound exudates may indicate a clinically relevant change in the wound state.

In another embodiment, color assessment of a disposable element within the device, or disposable electrodes within tube maybe possible. It may also be possible to map color profiles of exudates to pH. Several fluorescent nanoparticles systems can change color based on pH. In addition, a conjugated polymer could be used to do the same (redox potentials will change based on the pH of the local environment).

Additionally, it is possible to have a color changing element in contact with the exudates that is responsive to local pH changes and a reusable reader element that can analyze the pH changes via monitoring color response of the color changing element.

Temperature is useful for assessing bleeding events as well as to monitor for infection. Core blood is generally warmer than the interstitial fluids in the dermis. In general, embodiments using a disposable metallic element for measuring temperature values, as well as embodiments with reusable probes are envisaged.

In one aspect of the present invention, near infrared spectroscopy/visible spectroscopy may be used to detect the values of oxygen in hemoglobin present in wound exudates. The presence of oxygen may indicate the presence of hemoglobin, and therefore blood. In aspects of the present invention this could trigger an indicator, or cause one of the pinch mechanisms described herein to clamp a wound drain line to prevent further bleeding. In yet other embodiments, this event would provide a caregiver with appropriate treatment guidelines.

Tone and/or luminocity may be used to describe the color of the exudates. Changes in tone and/or luminocity may be indicative of changes in the physiological state of a wound and its stage of healing. A quantification system for evaluating the wideband absorption spectrum may also be useful for assessing the color and tone of the exudate.

In one embodiment, a wound system may include one or more laser diodes that provide very narrow wavelengths used to perform measurements. In this case a spectral map and/or vector can be generated by using a single detector in combination with multiple laser diodes and/or one or more scanning laser diodes. A scanning laser diode can produce a modulated wavelength through modulation of the driving signals produced by the drive electronics. Such modulation makes for simplified removal of artifacts caused by ambient light interference, movement and the like.

Figure 22:
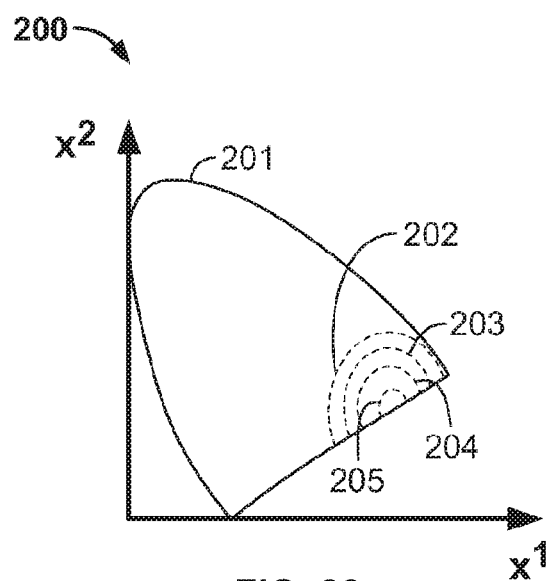
FIG. 22 is an exemplary two-dimensional vector map representing a range of wavelengths measured during spectral analysis of wound exudate, in accordance with an embodiment of the present invention.
Figure 23:
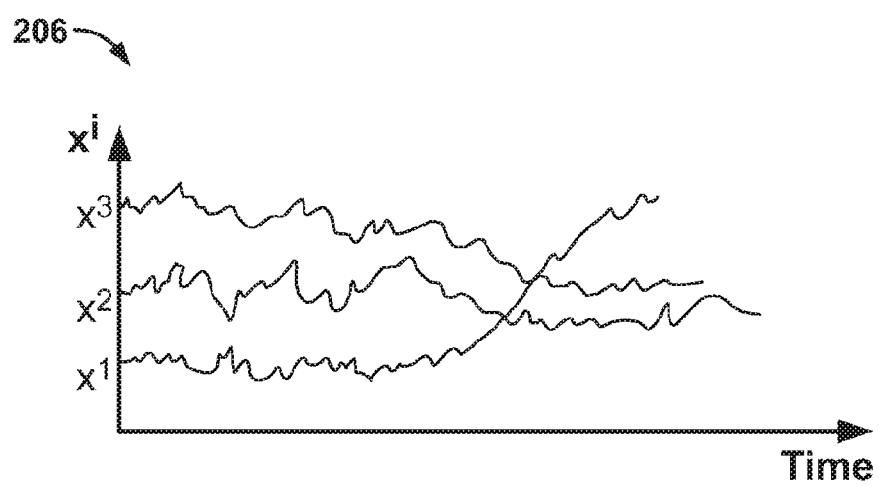
FIG. 23 is a spectral graph of the measurements of the map of FIG. 22, in accordance with an embodiment of the present invention.
Figure 24:
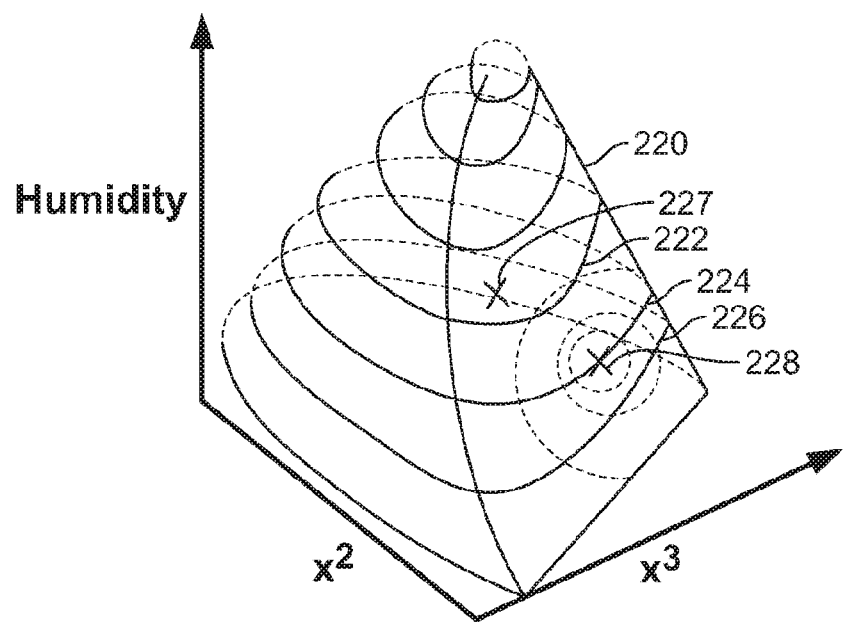
FIG. 24 is an exemplary three-dimensional vector map representing a range of wavelengths measured during spectral analysis of wound exudate, in accordance with an embodiment of the present invention.

A method for quantitative, real time spectral detection and assessment may be a steady, pulsed or modulated near infrared spectroscopy or functional near infrared spectroscopy technique. It may use multiple wavelength spectroscopy and the like. In one case, a exudates system may include a color analysis system in combination with a white light source. A color analysis system may comprise one or more photodiodes in combination with one or more bandpass filters in order to provide separate responses for segments of the light spectrum. One or more outputs from each band are generated, with each output providing the spectral component of a vector. Output vectors can be mapped to exudates states, thereby creating vector maps useful for determining the state of the exudates and thus, statements about the physiological condition of the wound, as seen in FIGS. 22-24.

Figure 20:
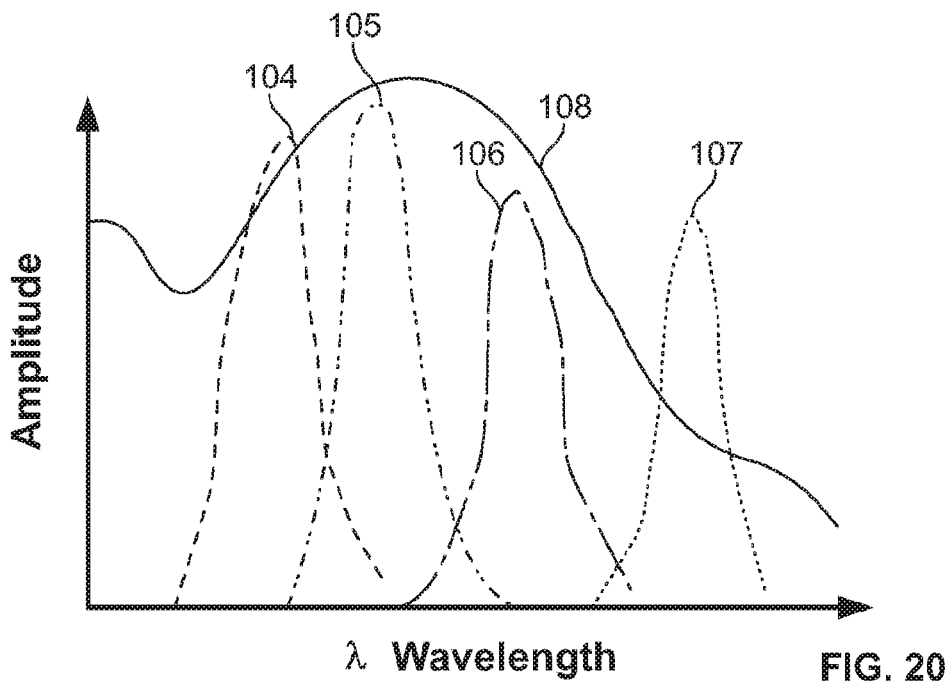
FIG. 20 depicts a graph showing different spectral intensities, in accordance with an embodiment of the present invention.

FIG. 20 is one example of an absorption map or tone map for analyzing different absorption wavelengths. As depicted in FIG. 20, by representative example only, a two-dimensional map shows absorption of a source spectrum 108 along a blue 104, yellow 105, red 106, and NIR 107 wavelength. This particular example depicts broadband detection for the colors indicated. However, alternative embodiments, a single broadband detector could also be used. Particular values seen in an absorption map can be translated into a particular assessment of a wound state. By way of example only, a process performed by the processor may be encoded to signal an alarm or pinch a drain line if a particular tonal color reaches a certain level.

Figure 21:
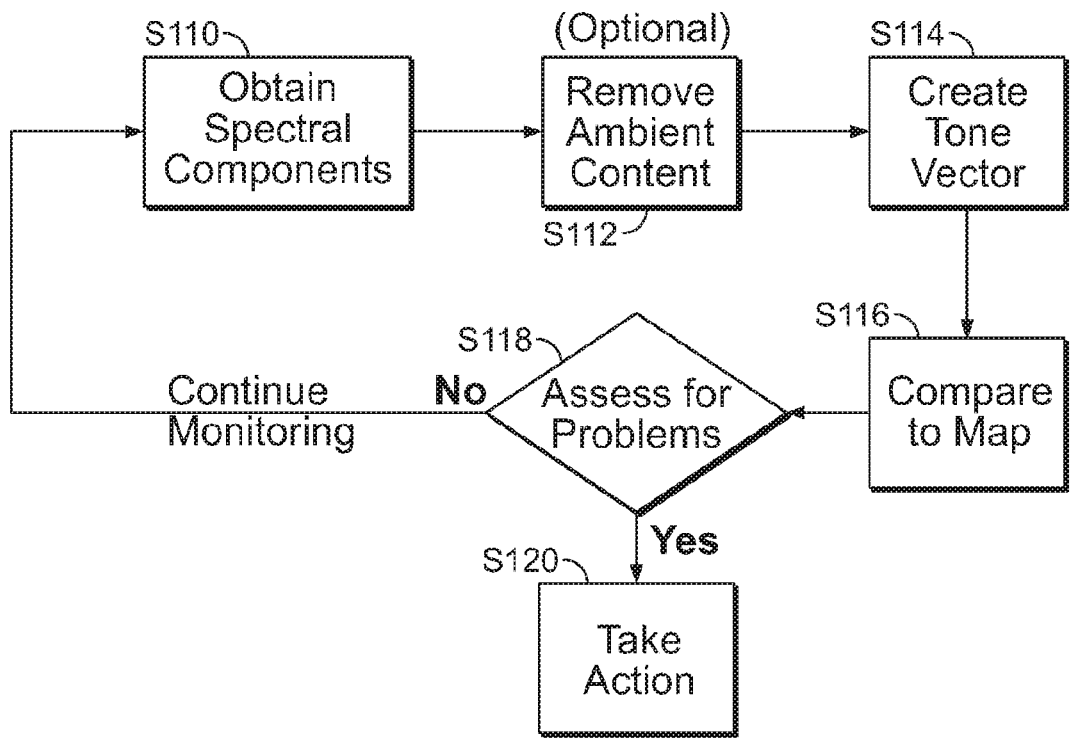
FIG. 21 is a flow diagram, of a process for spectral analysis of wound exudate, in accordance with an embodiment of the present invention.

FIG. 21 depicts a flow diagram of various operations performed to assess the color or tonal characteristics of a wound exudate. An initial block S110 may obtain various spectral components. Next, any ambient light may be removed in block S112 to increase the accuracy of any spectral readings from the wound exudate. Once block S112 is completed, tone vectors are calculated in block S114 from the readings obtained from block S110. Tone vectors may be calculated by any means known in the art. However, in preferred embodiments, the vectors may be calculated using the following equation:

$$\delta = \sum_{i=1}^{N} A_i \chi^j \qquad \text{Equation 1}$$

Equation 1 is a linear weighting equation that casts portions of the sensor spectrum (each portion indicated by a coordinate $X^i$) into an nth order vector space. Each portion of the spectrum is weighted by a scalar weighting parameter $A_i$ (in this example only, more generally the weighting parameters may be equations, or algorithms that better map responses into the vector space, adjust for subject parameters, as well as adjust for changes in ambient conditions).

The relationship computed in the equation may be used to map readings from individual sensors, wavelengths, and/or spectral bands into the nth dimensional figures, as disclosed herein. This process may be done to essentially create a map of the input responses into a quantifiable space such that diagnostic information may be more readily extracted from the collection of input signals. So for example, delta maps into this Nth order space, regions of which may have statistically significant relationships to various disease states, contraindications for the existing therapy, etc. By correlating where patient data falls on the map, and examining the historical data and trending data, the technology can assist in decision making with regards to therapeutic decisions.

These tone vectors are then compared to a tone map block S116 containing standard or acceptable tonal values. In assessing for any potential problems block S118, the tone vectors from block S114 are compared to the accepted values in block S116. If any of those values fall short of or exceed the acceptable ranges from block S116, a predetermined action in block S120 is performed. A programmed action may include, triggering an audible alarm from actuating one of the latch mechanisms described herein.

In particular, luminocity and tone may be indicative of infection, bleeding or increased edema in a wound, all conditions requiring urgent attention. Certain embodiments of the present invention may compare and analyze detected tone and luminocity values with predetermined values of tone and luminocity to provide a patient or caregiver with valuable treatment guidelines (see FIGS. 22, 23, and 24). Values of these various parameters may be combined into vector maps.

FIG. 22 is a two-dimensional vector map 200 based on a range of colors at a given luminocity 201, measured from the wound exudate. Map 200 represents data points along the spectral graph 206, as shown in FIG. 23. Different locations on the vector map 200 may indicate the likelihood or actual occurrence of various events related to wound state. For example at location 202 a normal exudate trend may be indicated, while locations 203 and 204 may indicate suspected bleeding or a high probability of bleeding, respectively. Location 205 may indicate the presence of an actual bleeding event. Graph 206 in FIG. 23 represents a line graph of three individual spectral profiles over a given period of time.

FIG. 24 is a three-dimensional vector map, similar to the two-dimensional map shown in FIG. 22, which is based on a range of colors measured from the wound exudate. Spectral components of wound exudate translated into vectors, may be mapped in such a two or three-dimensional map. By increasing the number of color channels, and therefore the number of wavelengths able to be detected, the sensitivity and accuracy of the system can be improved. Various points along the vector map, whether two or three-dimensional, may also indicate a trend of wound health. For example curve 220 may indicate an initial trend while curve 222 may indicate a slight progression towards infection. Curve 224 may indicate the actual onset of infection while curve 226 may indicate various regions with a probability of infection.

Given points, (e.g., 227 and 228) in the vector map may indicate a certain wound state. Such a wound state may correspond to a prescribed treatment guideline. These treatment guidelines may include, but are not limited to varying the settings of an NPWT, or closing off a wound drain. Presence of bacteria or other infection may necessitate administration of antibiotics to the patient.

Qualitative analysis of the color spectrum of wound exudates may be another valuable tool for assessing wound health. Table 2 depicts various exudates, their color, transparency and possible clinical indications.

TABLE 2

| Type of Exudate | Color, Transparency | Viscosity | Indications |
| --- | --- | --- | --- |
| Serous-transudate | clear, straw colored, | low viscosity, watery | normal (good) |
| Fibrinous | cloudy | low viscosity, strands | contains fibrin |
| Sero-sanguinous | clear, pink | low viscosity, watery | normal (good) |
| Sanguinous | red | low viscosity and watery | blood vessel trauma |
| Sero-purulent | murky yellow to creamy coffee | high viscosity | infection |
| Purulent | yellow, grey, green | high viscosity | presence of inflammatory cells, infection, pyogenic organisms |
| Hemo-purulent | Dark, red, | high viscosity and sticky | established infection, presence of neutrophils, bacteria, inflammatory cells with blood leakage due to vessel damage |
| Hemorrhagic | Red | thick | infection with trauma |

Practically, when considering diagnostic and treatment options for a patient suffering from a wound, in general, a clinician does not want to Joe inundated with data. It is desirable that an exudate assessment system analyze values detected from a wound, and provide decision support for the user regarding treatment options, rather than just data presentation. To that end, the system of the present invention is capable of analyzing the values of the data obtained from the sensors and/or detectors. Once an analysis is conducted the system may provide an assessment of the wound, as well as treatment guidelines.

Figure 28:
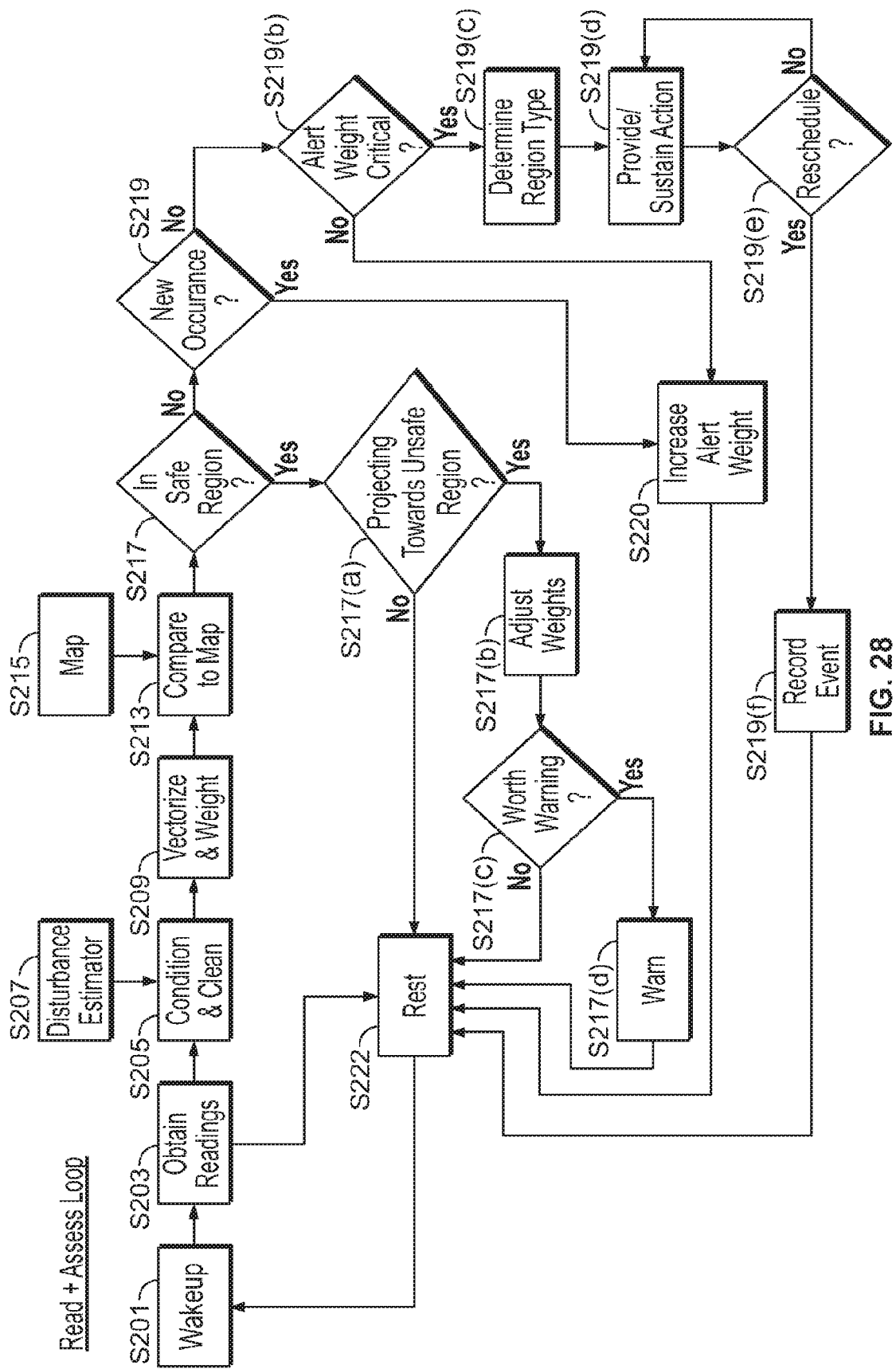
FIG. 28 is a flow diagram illustrating the steps in a read and assess loop process, in accordance with an embodiment of the present invention.
Figure 29:
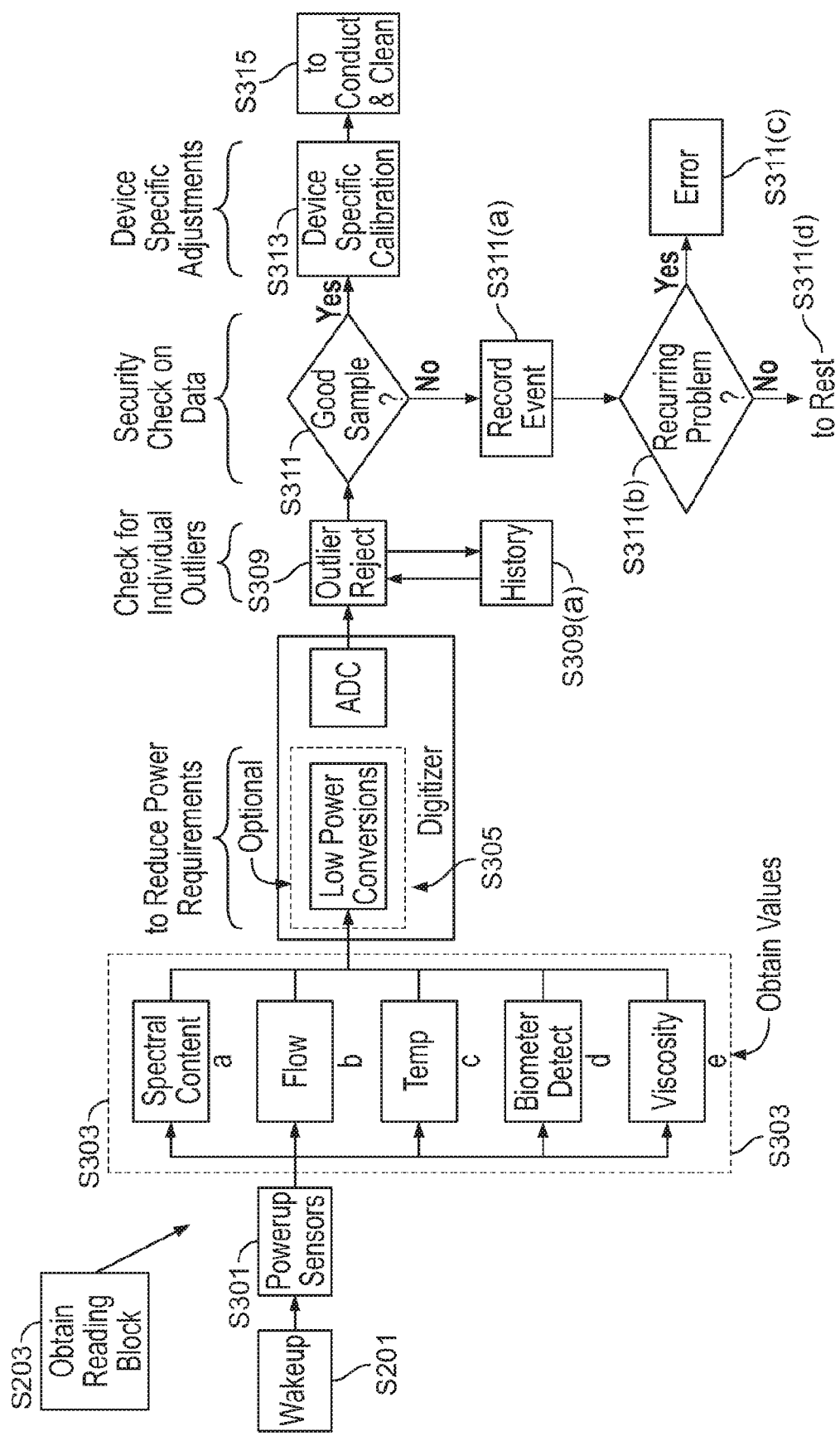
FIG. 29 is a flow diagram illustrating a process for obtaining readings of wound exudate, in accordance with an embodiment of the present invention.

Embodiments of methods and apparatuses according to the present invention may detect values of various parameters in real time, and perform analyzing processes as shown in FIGS. 28 and 29. These analyzing processes provide not only real time detection, which gives a much more accurate and reliable assessment of the wound, but also gives real time treatment suggestions, as they evaluate the current state of a wound, and not exudate that has been sitting in a collection canister for an extended period of time.

The exudates system may comprise processing components to perform various processes that provide or output a wound state condition or treatment option, which may include, among other things, microelectronic circuits such as discrete circuits, microcontrollers, microprocessors, ASICs, FPGAs or the like, to condition and analyze sensor data to meaningfully interpret the physiological parameters of the exudates. The processing components may be located integrally within the system so that the sensors, light sources and processing components are all contained within the same device. In an alternative embodiment, the processing components may be remotely located from the other parts of the system.

The process performed for analysis are generally adaptive and may be based on, one or more of the following: an averaged one-dependence estimators (AODE), Kalman filters, Markov models, back propagation artificial neural networks, Baysian networks, basis functions, support vector machines, k-nearest neighbors algorithms, case-based reasoning, decision trees, Gaussian process regression, information fuzzy networks, regression analysis, self-organizing maps, logistic regression, time series models such as autoregression models, moving average models, autoregressive integrated moving average models, classification and regression trees, multivariate adaptive regression splines. The sensor data may be analyzed from multiple sources using sensor fusion approaches. The specific process may be evolved using supervised learning, unsupervised learning, and/or reinforcement learning approaches. In addition, the device may comprise associated power sources and the like to drive the onboard electronics (sensors, microelectronic circuits, communication elements).

When tone and luminocity values are analyzed in combination with temperature readings, flow rate and NIR readings, a comprehensive statement may be made about the actual state of the exudates. By applying the processes described above to the various physiological parameters, including tone, luminocity, temperature and flow, a clinically appropriate set of treatment guidelines may be delivered by the system, thus eliminating the need for the caregiver or patient to have to interpret large amounts of data and make a subjective determination.

FIG. 28 is a flow diagram of an exemplary process to obtain and analyze parameter readings, as well as present and display warnings and treatment options.

The process of FIG. 28 is also referred to as a read and assess loop. The wound monitoring system may be at a sleep state to reserve or reduce power consumption. The system may be "woken up" during a wake-up phase S201, in response to some input. This input may be any type of stimuli such as motion, or as a result of a timer. Once awake, the system will obtain parameter readings S203. After block S203, the device may immediately return to a rest state in block S222. If this is the logic path followed by the device, the readings obtained in block S203 may also be stored in a memory.

If after obtaining readings in block S203, the system does not immediately return to rest 3222, the device may be conditioned and cleaned in block S205 In the first mode from wake up, the device may be in a loop where it simply wakes up takes a reading, potentially stores it and then rests, as already described. If instead of resetting, the device needs to switch modes to monitoring disturbances from block 207 it will need to activate a conditioning function, which may be there to obtain the raw signals from 207 and prepare them for analysis (e.g., converting from analog to digital signals depending on sensor type or other forms of data conversion/ signal conditioning know in the art). It may also be necessary to clean the signals because many signals can have "noise" or spurious data which may need to be filtered out before processing in 209.

If after obtaining readings in block S203, the system does not immediately return to rest S222, the device may be conditioned and cleaned in block S205. This cleaning step aids in obtaining an accurate reading and filtering out any extraneous data or artifacts. After blocks S205 the readings obtained in block S203 are converted to vectors and assigned a corresponding weight S209. The weighting of the various readings can be based on any factor known in the art. By way of representative example only, one parameter such as temperature may be given a higher weight than pH, or vice versa. Such weighting can be changed from patient to patient or as applied to the same patient. Such weighting may also be assigned based on historical weights of various parameters. Once the readings are vectorized and weighted, the processor in block S213 compares the vectorized and weighted values to a vector map. At this point, the processor analyzes the data, and makes a determination, based on the vector's location on a vector map, as to whether the value is in a safe region in block S217. What constitutes a safe region is also a parameter that may be predetermined and stored in a memory associated with the processor. If, it is determined in block S217A the readings are in a safe region but appear to be trending toward an unsafe region, the weights of those readings may be adjusted in block S217(*b*) to assign a higher priority to said values. Next, based on the adjusted weights, the system makes a determination as to whether or not it is worth warning a user S217 (*c*) of the trend toward an unsafe region. If based on predetermined values, the processor determines that it is in fact worth warning a user, then a warning is issued in block S217(*d*). If not, the system returns to the rest state in block S222 for power minimizing consumption.

If the vectorized, and weighted reading is not in a safe region, the processor determines whether or not the unsafe reading is a new occurrence in block S219. If it is a new occurrence, the alert weight of the occurrence is increased in block S220. Once the alert weight is increased, the processor returns to the rest state S222. If the device or processor determines that the unsafe reading is not a new occurrence, a determination is made as to whether the alert weight is critical in block S219(*b*).

If the alert weight is not critical, then the alert weight is merely increased in block S220 and the device returns to rest state S222. If the alert weight is critical, the processor determines in block S219(*c*) which region of the vector map the value falls in and what type of condition is therefore indicated by the value of the readings. Based on the region and type of event detected at in block S219(*c*), an action is initiated in block S219 (*d*). An action may be an alert, an alarm, a pinching of a wound drain, or any other type of event or warning, which aids the user in assessing or treating the wound. If the action taken at block S219(*d*) is resolved, as determined in block S219(*e*) the device and/or processor will record the event in block S219(*f*) and return to rest S222. If the event has not been resolved, the action at block S219(*d*) will be repeated or sustained.

At block S203 at the read and assess loop, readings are obtained. FIG. 29 is a detailed logic diagram of operations performed in block S203. Once the processor or device "wakes up," the sensors 301 are then powered up. Once the sensors are powered up, parameter values may be obtained S303. As depicted in FIG. 29, parameters such as spectral content of the wound exudate S303(*a*), flow S303(*b*), temperature S303(*c*), biomarker detection S303(*d*), and viscosity (e) are detected and measured. While these parameters are illustrated in FIG. 29, they are by way of representative example only and the current invention can be used to measure any parameter present in wound exudate. These values are then converted to digital signals in block S305, which may be done as a low power conversion to reduce power requirements. Once the values nave been digitized, the processor in block S309 performs a check for values that may be statistical outliers.

At block S309, as part of the outlier analysis, the values may be stored in a memory to be incorporated into the historical data S309 (*a*). If the sample is determined to be a good sample in block S311, the processor will perform a specific calibration S313 to adjust to the specific present conditions. Once this adjustment is performed, the processor in block S315 may perform the conditioning and cleaning similarly as in step S207. If the sample is determined by the processor in blocks to not be a good sample, the event is recorded in block S311(a). If the bad sample is a recurring problem, which may be detected by prior historical values, an error message is displayed to the user in block 311(c). If the problem sample is not recurring, the processor returns to rest S311(d).

After the processor has determined the wound state and/or treatment information, that data may be provided or communicated to a user or patient. As discussed above, the system is capable of communicating or providing values and treatment guidelines to a user. In addition, the system is also capable of communication directly with a negative pressure wound therapy device in order to effectuate necessary changes.

The system comprises means for alerting a patient or caregiver to the presence of an abnormal state, quantity, or condition of the exudates. In this case, it may comprise one or more lights, a display, a speaker, a vibrating element, or similar in order to communicate information to a patient or caregiver.

The device may further include wireless communication capabilities so as to deliver relevant information about the wound exudates to the NPWT device. Such information may include the presence of blood in the exudates, the presence of bacteria, a change in the absorption spectrum of the exudates, a change in the flow race of the exudates, and the like.

Results of the wound assessment may be displayed through any type of graphical user interface, monitor or other type of display. Results of wound assessment may also be conveyed to a clinician and/or patient by the use of indicators as seen. Indicators may be any visual indicators such as lights, or audible indicators such as buzzers or alarms, or a haptic communication device such as a vibration motor to alert the clinician or patient when a particular event has been detected.

The exudates system may comprise a means for communicating via a network such a cellular network, a wireless personal area network (WPAN), wide area network (WAN), metropolitan area network (MAN), local area network (LAN), campus area network (CAN), virtual private network (VPN), internet, intranet or near-me area network (NAN).

The exudates system may be arranged as a node in a network, thus providing an element in a ring, mesh star, fully connected, line, tree or bus network topology. In one embodiment the exudates system communicates relevant values and as a node in a mesh or star network topology.

The exudates system may comprise means for interfacing with a local telecommunications network, such as a cellular network via a locally positioned mobile handset, a wireless node, a wireless modem, phone adaptor or the like.

The exudates system may communicate relevant information through the network using various protocols such as IrDA, Bluetooth, UWB, Z-WAVE, ANT, or ZigBee. Preferably, the relevant information is sent via low power protocols such as Blue tooth low energy, ANT or ZigBee.

The exudates system may comprise an integrated power switch such that power is automatically provided to the onboard microcircuitry as soon as the system, or a wound device with which the system is associated, is positioned so as to effectively assess exudates. In another embodiment, the system may comprise a proximity sensor to awaken the system itself or wound device from sleep. The sleep function may be useful to reserve power during periods of nonuse.

Figure 7:
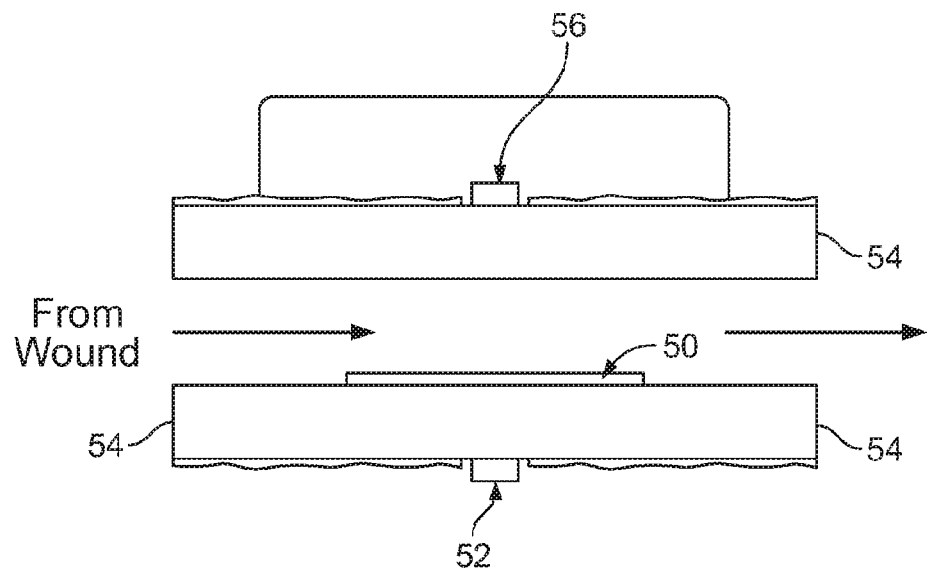
FIG. 7 depicts a wound exudate system containing an inflow feature with a biomarker coating, in accordance with an embodiment of the present invention.

In another embodiment, the system may include a wound dressing with fluorescent biomarkers as shown in FIG. 7. Biomarkers 50 may be employed for detecting various conditions. Biomarkers 50 can be assessed by externally positioned optical sensors 52, thus providing a non-contact way to assess exudates properties. The optical sensors 52 can use colorimetric analyses to read the biomarkers 50 and detect the presence, absence or quantity of a particular value of a physiological parameter. In one embodiment, an optional light source 56 may be used to emit light into the wound exudate.

In this particular embodiment, optical sensors 52 may be located on the outer surface of an opaque, or optically transparent tube 54. Biomarkers can change based on local pH, local impedance, local redox potentials, color, and can fluoresce based on certain criteria, all of which are known in the art. As they interact with the exudates they are useful to detect the presence or absence of certain biological materials. The exudates system may read, detect or assess the biomarkers through optical means (color change, fluorescence, etc.), or electrical means (pH, redox, impedance, etc.).

In yet another embodiment, the system may detect presence of an infection, including but not limited to methicillin resistant *Staphylococcus aureus* (MRSA) or vancomycin resistant enterococci (VRE), to alert a patient at home that they need in-patient hospital treatment. These various infections may be detected by assessing biomarkers integrated within the system, or by assessing the value of other physiological parameters, including but not limited to temperature.

In one preferred embodiment, each process performed by the system can be done in a non-contact fashion such that the sensors and electronics supporting the sensors do not come into contact with the exudates. This allows the components of the system to be reused, as cross contamination is avoided, thus sparing the expense of having to use replaceable sensors with each use.

Figure 17:
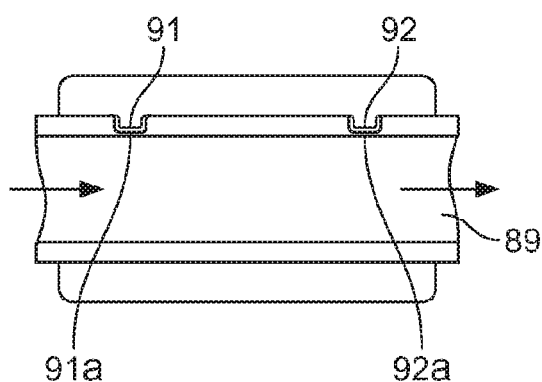
FIG. 17 depicts an embodiment of a wound exudate system containing thin membranes with pressure sensors disposed thereon, in accordance with an embodiment of the present invention.
Figure 18:
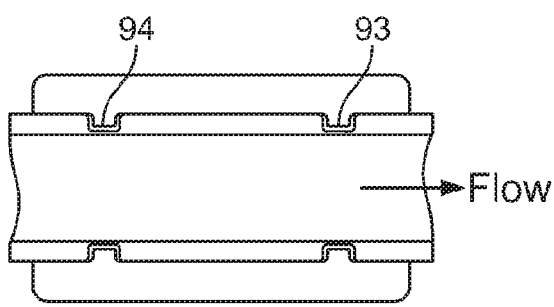
FIG. 18 depicts a wound exudate system containing thermal mass sensors, in accordance with an embodiment of the present invention.

Non-contact is defined herein as not having direct contact between the fluid under analysis, and the sensory elements. Thin membranes in the drainage lines can be used to sense pressure, temperature, etc. (see FIG. 17). FIG. 18 depicts an alternative embodiment, of a wound exudate system, which contains pressure sensors. In the present embodiment, the wound exudate system may contain two sections adjacent to a wound drain 89. Those two regions are indicated in FIG. 17 as 91 and 92 at the interface of the system and the drain where the wall thickness of the system is reduced. At the precise interface between the system and the wound drain, a thin membrane is disposed thereon (not shown). The thinner membrane allows pressure sensors to detect a pressure inside the drain at locations 91a and 92a. A pressure $P_1$ is assigned to a pressure reading at location 91a and a second pressure $P_2$ is obtained for the pressure reading at location 92a. The difference between these two pressure readings can be used to establish, for example, flow rate, viscosity. The configuration described above may be self-contained within a disposable shunt for placement over an existing wound drain line, or designed as an integral component of a wound drain line.

FIG. 18 depicts an embodiment similar to that as seen in FIG. 17. However, the embodiment depicted in FIG. 18 measures thermal mass vis-à-vis a microheating element disposed in each of recesses 93 and 94. This embodiment may be useful to estimate flow rates along the wall of a wound drain line.

The exudates system may comprise a means for pinching off, or otherwise closing a wound drainage line in the event of an anomaly (such as the presence of blood in the exudates. In this case, the device may comprise an actuator that may be deployed so as to squeeze the line during an adverse event. In another case, the actuator may be arranged such that it is forcefully retracted during normal operation and is released during an adverse event, thus clamping down onto a wound drain line and pinching off fluid flow.

FIGS. 9-16 depict various control mechanisms for controlling or stopping the flow of any fluid from a wound. These control mechanisms may include pinch lines to control the flow of exudates upon detection of a certain physiological value. These pinch mechanisms may also be referred to herein as latches. Different types of latches may be activated by different mechanisms. In one mechanism, the latch is an active material element that will change shape in response to a stimulus. Suitable active materials include shape memory alloys, electroactive polymers, piezoceramics, etc. In this particular embodiment, the active material latch is designed such that it releases upon stimulation.

If used as part of an NPWT system in response to a certain parameter value, the system may pinch the wound drainage line so as to force a fault (blocked line fault) on the NPWT device. In this case, the system need not have its own means for alerting the patient or caregiver of an adverse event, but rather may trigger an alarm that is present in existing NPWT devices to achieve this goal.

Figure 15:
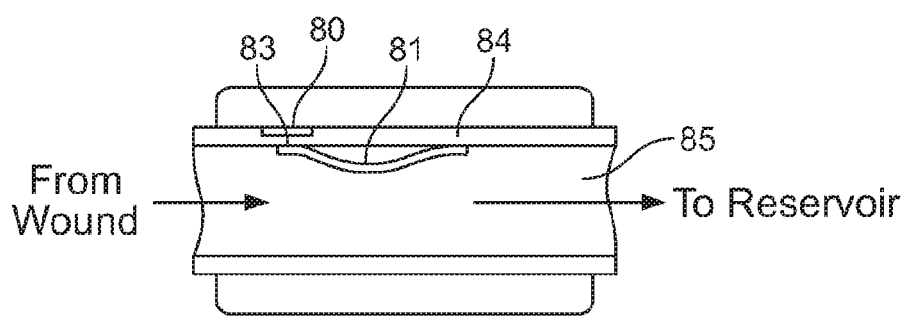
FIGS. 15 and 16 depict a wound exudate system configured with a resistive heat break element in a not applied state and an applied state, respectively, in accordance with an embodiment of the present invention.
Figure 16:
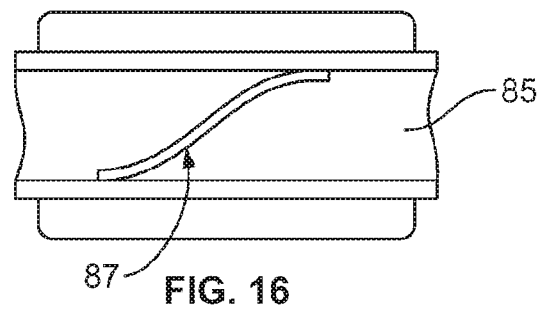

In another embodiment, a suitable latch is designed with an integrated resistive heating element 80, a reed 81 and a disbondable fastened region 83, as seen in FIG. 15. The reed is deformed during manufacturing and bonded with the disbondable fastened region 83 in the deformed state. The reed is also bonded to an attachment point 84, in which the bond is not broken. The latch system is designed such that fluid can flow through an adjacent channel when the reed is held to the disbondable region, but that fluid flow through the channel on fluid line 85 may be blocked when the reed is released 87. Upon heating of the heating element 80, the disbondable fastened region 83 melts, deforms, or vaporizes, causing the deformed reed to break away from the fastened region 83. During this process, the reed bridges the fluid line 85, as shown in FIG. 16, preventing flow and optionally triggering a blockage alarm. Other alternative latch designs will be evident to someone skilled in the art.

The wound drain may have a particular shape so as to maintain laminar flow of the exudate during suction, in addition to providing for an actuating means for pinching off a wound drain line in the event of an adverse event such as bleeding. Representative examples of this embodiment can be seen in FIGS. 9 and 10. The mechanical elements present in this embodiment are comprised of a solenoid based pinch valve 65. As with traditional solenoid based apparatuses, the pinched valve 65 of the present embodiment contains a coil magnet 66 and a coiled actuator magnet 67. In the present embodiment, the pinched valve may be actuated to close or substantially narrow the interior wall of the wound drain 69.

Figure 10:
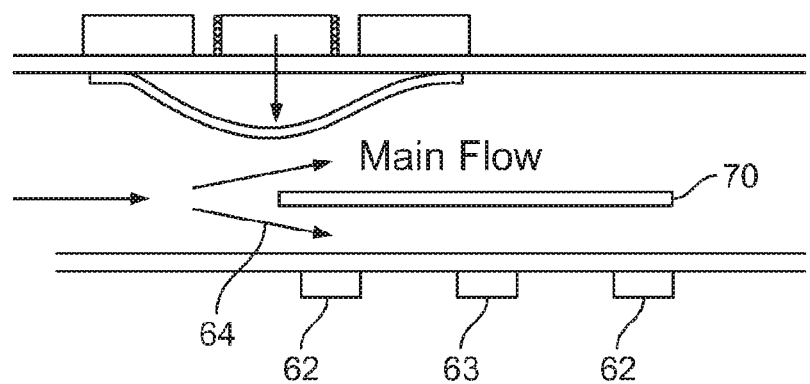

This change of the channel width of the wound drain assists in detecting laminar to turbulent flow and may restrict flow for better analysis or measurement. The embodiment depicted in FIG. 9 may be combined with any of the other embodiments described herein, such as a flow disruption element 70 as shown in FIG. 10. When flow disruption element is present, analysis and detection may take place along an analysis flow region 64 by sources 62 and detectors 63.

Figure 11:
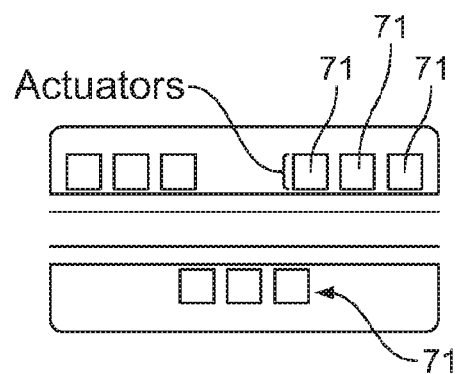
FIG. 11 depicts a wound exudate system with multiple actuators for pinching a wound drain line, in accordance with an embodiment of the present invention.
Figure 12:
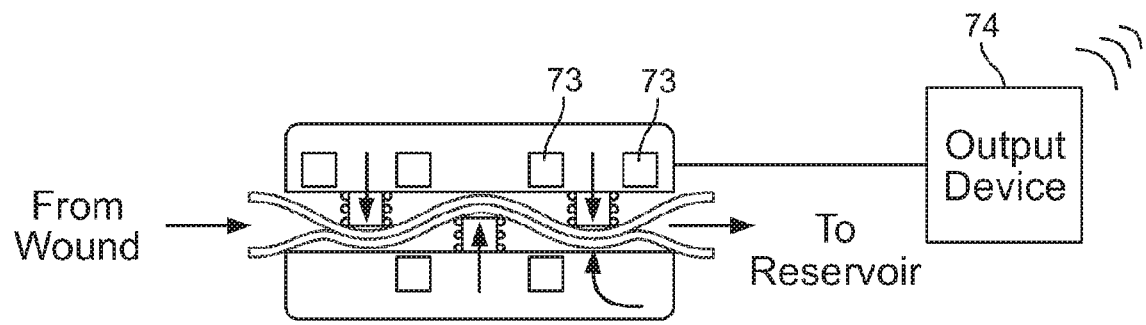
FIG. 12 depicts an alternative embodiment of a wound exudate system having multiple pinching mechanisms disposed along opposing sides of a wound drain line, in accordance with an embodiment of the present invention.

As seen in FIG. 11, more than one solenoid 71 actuator can be used to enhance the pinching affect. FIG. 12 depicts an alternative embodiment wherein multiple pinching actuators 73 are disposed on opposite sides of a wound drain line. The actuators 73, depicted in FIG. 12 can be activated in response to a stimulus, such as the presence of blood. In the event the actuators 73 are activated and pinch the drain line to prevent further bleeding. An alarm 74 can signal a blocked flow line.

Figure 13:
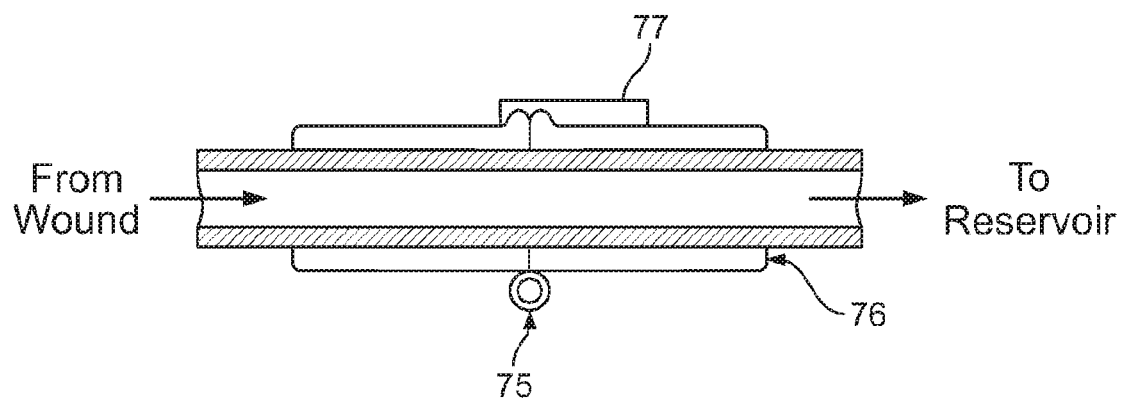
FIGS. 13 and 14 depict an alternate embodiment of a wound exudate system containing a spring loaded latch in a secured state and released state, respectively, in accordance with an embodiment of the present invention.
Figure 14:
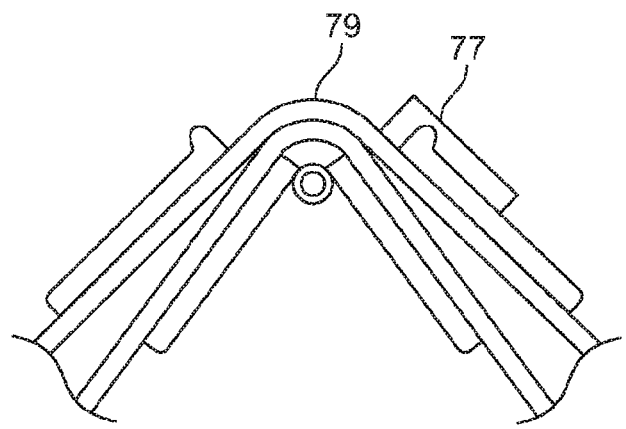

FIG. 13 depicts yet another embodiment of the present invention containing a spring loaded, resettable latch. Upon actuation, the spring loaded latch releases and causes the mechanism to pinch the wound drain line 79 in the event of the detection of some unwanted occurrence, such as bleeding, as shown in FIG. 14. The spring loaded element 75 once actuated can be reset and the latch 77 may be re-secured, as shown in FIG. 13. In this particular embodiment, electronics and power sources necessary for operation may be contained on an external housing.

In the case of a conventional dressing or bandage, the dressing component may be modified so as to easily integrate with the exudate assessment system. To enable this integration, the dressing may have electrical traces as an interface. The electrical traces may be printed using electroconductive inks (Ag, AgCl, C, Ni, etc.), or formed via several available RFID techniques known in the art, and embedded for electrically Interacting with the exudate assessment system.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for assessing wound exudate from a wound of a patient, said system comprising:
    a wound treatment device;
    a wound drain line for the passage of wound exudate, the wound drain line comprising a lumen and including an interior wall that at least partially defines an internal channel that is sized for the passage of wound exudate;
    an actuator positioned relative to the wound drain line to control wound exudate flow, the actuator positioned to act directly on the interior wall to vary a width of the internal channel and thereby control wound exudate flow;
    a sensor or detector for detecting one or more values of one or more physiological parameters of the wound exudate; and
    a processor for analyzing the values of the one or more physiological parameters so as to obtain an assessment of the wound exudate and provide a treatment guideline based on the assessment;
    wherein the wound treatment device, the sensor or detector, and the processor are integrated.

2. The system of claim 1, in which the wound treatment device is a negative wound pressure therapy device.

3. The system of claim 2, further comprising a controller to control the negative pressure wound therapy device using the treatment guideline.

4. The system of claim 1, in which the wound treatment device is a dressing or a bandage.

5. The system of claim 4, further comprising an electrical trace integrated with the dressing or bandage.

6. The system of claim 1, in which the processor is operable to transmit the treatment guideline to an external device located remotely from the system.

7. The system of claim 1, in which the values of the one or more physiological parameters include luminosity values.

8. The system of claim 1, in which the values of the one or more physiological parameters include tone values.

9. The system of claim 1, in which the detector and the processor are arranged to be isolated from the wound exudate.

10. A system for assessing wound exudate from a wound of a patient, said system comprising:
a wound treatment device;
a wound drain line for the passage of wound exudate, the wound drain line including an interior wall that at least partially defines an internal channel that is sized for the passage of wound exudate, the wound drain line arranged to conduct wound exudate therethrough in a first direction;
an actuator positioned relative to the wound drain line to control wound exudate flow, the actuator positioned to act directly on the interior wall to vary a width of the internal channel and thereby control wound exudate flow;
a flow disruption element positioned within the internal channel and spaced from the interior wall, the flow disruption element arranged to extend lengthwise within the internal cavity parallel to the first direction;
sensors or detectors to detect or sense one or more values of one or more physiological parameters of the wound exudate; and
a processor to analyze the values of the one or more physiological parameters so as to obtain an assessment of the wound exudate and provide a treatment guideline based on the assessment;
wherein the wound treatment device, the sensors or detectors, and the processor are integrated.

11. The system of claim 1, further comprising a second actuator arranged around the wound drain line to restrict wound exudate flow by clamping onto the wound drain line.

12. The system of claim 1, wherein the actuator comprises a solenoid-based pinch valve.

13. The system of claim 1, comprising a plurality of actuators.

14. The system of claim 1, wherein the actuator is activated in response to a stimulus.

15. The system of claim 1, wherein the actuator is in communication with the processor such that the actuator may control the flow of wound exudate from the wound upon detection of the one or more values of one or more physiological parameters of the wound exudate.

16. The system of claim 2, wherein the actuator is in communication with the negative pressure wound therapy device.

17. A system for assessing wound exudate from a wound of a patient, said system comprising:
a wound treatment device;
a wound drain line for the passage of wound exudate, the wound drain line including at least one interior wall that at least partially defines an internal channel that is sized for the passage of wound exudate;
a plurality of actuators positioned relative to the wound drain line to control wound exudate flow, each actuator positioned to act directly on the at least one interior wall to vary a width of the internal channel and thereby control wound exudate flow, the plurality of actuators including a first actuator disposed on a first side of the wound drain line and a second actuator disposed on a second side of the wound drain line opposite the first side, the first and second actuators being spaced apart from one another along a length of the wound drain line;
a sensor or detector for detecting one or more values of one or more physiological parameters of the wound exudate; and
a processor for analyzing the values of the one or more physiological parameters so as to obtain an assessment of the wound exudate and provide a treatment guideline based on the assessment;
wherein the wound treatment device, the sensor or detector, and the processor are integrated.

* * * * *